US007655428B2

(12) United States Patent
Valkirs et al.

(10) Patent No.: US 7,655,428 B2
(45) Date of Patent: Feb. 2, 2010

(54) LATENT PROTEIN C ASSAYS AND THEIR USES FOR DIAGNOSIS AND/OR PROGNOSIS IN SYSTEMIC INFLAMMATORY RESPONSE SYNDROMES

(75) Inventors: Gunars E. Valkirs, Escondido, CA (US); Joseph A. Buechler, Carlsbad, CA (US); Seok-Won Lee, San Diego, CA (US); Uday Kumar Veeramallu, San Diego, CA (US)

(73) Assignee: Biosite, Inc., Waltham, MA (US)

( * ) Notice: Subject to any disclaimer, the term of this patent is extended or adjusted under 35 U.S.C. 154(b) by 391 days.

(21) Appl. No.: 11/614,836

(22) Filed: Dec. 21, 2006

(65) Prior Publication Data
US 2007/0172906 A1    Jul. 26, 2007

Related U.S. Application Data

(60) Provisional application No. 60/753,688, filed on Dec. 22, 2005.

(51) Int. Cl.
| G01N 21/00 | (2006.01) |
| G01N 21/64 | (2006.01) |
| G01N 21/75 | (2006.01) |
| G01N 21/76 | (2006.01) |
| G01N 25/18 | (2006.01) |
| G01N 33/00 | (2006.01) |
| A61K 39/00 | (2006.01) |
| A61K 39/395 | (2006.01) |
| A61K 39/44 | (2006.01) |

(52) U.S. Cl. ............ 435/7.93; 435/4; 435/7.1; 435/7.92; 436/149; 436/164; 436/172; 422/68.1; 422/82.01; 422/82.05; 422/82.06; 422/82.07; 422/82.08; 424/130.1; 424/133.1; 424/141.1

(58) Field of Classification Search ............... None
See application file for complete search history.

(56) References Cited

U.S. PATENT DOCUMENTS

| 5,460,953 | A | * | 10/1995 | Gerlitz et al. ............... 435/226 |
| 5,965,375 | A | | 10/1999 | Valkirs |
| 6,207,395 | B1 | | 3/2001 | Valkirs et al. |
| 6,503,722 | B1 | | 1/2003 | Valkirs |
| 6,828,110 | B2 | | 12/2004 | Lee et al. |

(Continued)

FOREIGN PATENT DOCUMENTS

WO    WO 2007/011722 A2    1/2007

(Continued)

OTHER PUBLICATIONS

McCoy et al., "Drotrecogin alfa (recombinant human activated protein C) for the treatment of severe sepsis," Clinical Therapeutics, 2003, vol. 25, pp. 396-421.*

(Continued)

Primary Examiner—Unsu Jung
(74) Attorney, Agent, or Firm—Wilson Sonsini Goodrich & Rosati

(57) ABSTRACT

The present invention relates to methods and compositions for measuring latent protein C in test samples, particularly patient samples. The methods and compositions described are sensitive for latent protein C, relative to activated protein C.

23 Claims, 2 Drawing Sheets

U.S. PATENT DOCUMENTS

| | | | |
|---|---|---|---|
| 6,908,739 | B2 | 6/2005 | Buechler et al. |
| 7,052,858 | B2 | 5/2006 | Gray et al. |
| 7,329,738 | B1 | 2/2008 | Lee et al. |
| 7,374,888 | B2 | 5/2008 | Valkirs et al. |
| 7,393,647 | B2 | 7/2008 | Valkirs et al. |
| 2003/0186862 | A1* | 10/2003 | Nelsestuen .................. 514/12 |
| 2005/0148029 | A1 | 7/2005 | Buechler et al. |
| 2005/0164238 | A1 | 7/2005 | Valkirs et al. |
| 2005/0196817 | A1* | 9/2005 | Kingsmore et al. ........ 435/7.92 |
| 2008/0050832 | A1 | 2/2008 | Buechler et al. |
| 2008/0124747 | A1 | 5/2008 | Valkirs et al. |
| 2009/0004755 | A1 | 1/2009 | Lee et al. |

FOREIGN PATENT DOCUMENTS

| | | | |
|---|---|---|---|
| WO | WO 2007011722 | A2 * | 1/2007 |
| WO | WO 2007/011722 | A3 | 6/2007 |

OTHER PUBLICATIONS

Chognot, et al. Identification of protein C epitopes altered during its nanoencapsulation. J Protein Chem. Oct. 1999;18(7):779-84.

International Search Report dated May 29, 2008 from PCT Application No. US2006/062517.

Macias, et al. Severe protein C deficiency predicts early death in severe sepsis. Crit Care Med. May 2004;32(5 Suppl):S223-8.

Mesters, et al. Prognostic value of protein C concentrations in neutropenic patients at high risk of severe septic complications. Crit Care Med. Jul. 2000;28(7):2209-16.

Vincenot, et al. A monoclonal antibody recognizing the activation domain of protein C in its calcium-free conformation. FEBS Lett. Jul. 31, 1998;432(1-2):94-7.

Yan, et al. Low levels of protein C are associated with poor outcome in severe sepsis. Chest. Sep. 2001;120(3):915-22.

Office action issued May 29, 2009 for U.S. Appl. No. 11/543,312.

* cited by examiner

LATENT PROTEIN C ASSAYS AND THEIR USES FOR DIAGNOSIS AND/OR PROGNOSIS IN SYSTEMIC INFLAMMATORY RESPONSE SYNDROMES

CROSS-REFERENCES TO RELATED APPLICATIONS

The present application claims priority to United States provisional application No. 60/753,688, filed Dec. 22, 2005, incorporated by reference in its entirety for all purposes.

FIELD OF THE INVENTION

The present invention relates to the identification and use of diagnostic markers related to Systemic Inflammatory Response Syndrome (SIRS) and/or sepsis. In various aspects, the invention relates to methods and compositions for use in assigning a treatment pathway to subjects suffering from SIRS, sepsis, severe sepsis, septic shock and/or multiple organ dysfunction syndrome.

BACKGROUND OF THE INVENTION

The following discussion of the background of the invention is merely provided to aid the reader in understanding the invention and is not admitted to describe or constitute prior art to the present invention.

Protein C (human precursor: Swiss-Prot P04070, Annotation Release 44, July 2004, which is hereby incorporated in its entirety herein) is a vitamin K-dependent serine protease involved in blood coagulation. Synthesized as a single chain precursor, protein C is cleaved into a light chain and a heavy chain connected by a disulfide bond. The "latent" form of the enzyme contains an "activation peptide" at the amino terminus of the heavy chain. Protein C is activated by thrombin/thrombomodulin-mediated cleavage of this peptide to produce active protein C (APC).

Protein C levels and/or function are affected by numerous pathological states, including inherited protein C deficiencies, activated protein C resistance, deficiencies of protein S, deficiencies of antithrombin, and acquired protein C deficiencies. The latter is caused by a variety of conditions, including disseminated intravascular coagulation, deep vein thrombosis, pulmonary embolism, and anticoagulant therapy. In systemic inflammatory response syndromes, the interplay of coagulation state and inflammation can result in decreased protein C activity, which has been reported to be of diagnostic and prognostic significance. Recombinantly produced human activated protein C (drotrecogin alfa, or XIGRIS® (Eli Lilly)) is the first drug approved by the U.S. F.D.A. for treatment of severe sepsis. See, e.g., Hosac, *BUMC Proceedings* 15: 224-227, 2002; Kinasewitz et al., *Crit. Care* 8: R82-R90, 2004; dePont et al., *Crit. Care* 9: R490-R497, 2005. Each of the foregoing is hereby incorporated in their entirety herein.

Assays for protein C generally fall into one of two classes: functional assays that measure the serine protease activity of active protein C, and immunological assays that detect total protein C. See, e.g., Axelsson, *Protein C Product Monograph* 1995, Chromogenix AB; Liaw et al., *J. Thromb. Haemost.* 1:662-70, 2003. Each of the foregoing is hereby incorporated in their entirety herein. These assays share certain common features: the ability to detect active forms of protein C, and a demonstrated relationship to diagnosis and prognosis of septic patients. In the presence of administered XIGRIS, however, such assays may not be reflective of the physiological state of the patient, as both XIGRIS and endogenous protein C will contribute to the assay signal obtained.

Antibodies that bind to protein C heavy chain but not to activated protein C have been described in the scientific literature. See, e.g., Takahashi et al., *Biochim. Biophys. Acta.* 1161:113-23, 1993; Vincenot et al., *FEBS Lett.* 432: 94-97, 1998. Each of the foregoing is hereby incorporated in their entirety herein. Although these antibodies have been reported to inhibit cleavage of the protein C heavy chain by thrombin/thrombomodulin, there is no report of immunoassays using such antibodies to detect latent protein C in patient samples, or that if such immunoassays were to be provided, such assays would be reflective of the physiological state of patients.

BRIEF SUMMARY OF THE INVENTION

The present invention relates generally to the measurement of latent protein C in patient samples, more preferably blood samples, and most preferably blood fractions such as serum or plasma. Such assays can be used for the detection of sepsis, the differentiation of sepsis from other causes of SIRS, and in the stratification of risk in sepsis patients.

In a first aspect, the invention relates to immunoassay methods for detection of latent protein C in a test sample obtained from a patient. These methods comprise contacting the test sample with an antibody that binds latent protein C, wherein the antibody is sensitive for latent protein C relative to activated protein C. A signal indicative of protein binding to the antibody is generated, and that signal is related to the presence or amount of latent protein C in the test sample.

In a related aspect, the invention relates to immunoassay methods for detection of latent protein C in a test sample obtained from a patient. These methods comprise contacting the test sample with an antibody that binds latent protein C, wherein the antibody specifically binds latent protein C relative to activated protein C. A signal indicative of protein binding to the antibody is generated, and that signal is related to the presence or amount of latent protein C in the test sample.

These methods can utilize labeled molecules in various homogenous, sandwich, competitive, or non-competitive assay formats, to generate a signal that is related to the presence or amount of latent protein C. Additionally, certain methods and devices, such as antibody-based biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirely, including all tables, figures and claims.

Certain preferred assays are sandwich immunoassays. In these immunoassay methods, a test sample is contacted with a first antibody conjugated to a solid phase and a second antibody conjugated to a signal development element, wherein one or both of the first and second antibodies are sensitive for, or specifically bind, latent protein C relative to activated protein C, and the signal generated is indicative of protein bound to both the first and second antibodies.

Other preferred assays are competitive immunoassays. In these immunoassay methods, a test sample is contacted with latent protein C conjugated to a solid phase and an antibody conjugated to a signal development element; or to latent protein C conjugated to a signal development element and an antibody conjugated to a solid phase. In each case, the antibody used is sensitive for, or specifically binds, latent protein C relative to activated protein C.

In another aspect, the invention relates to methods for determining a diagnosis and/or a prognosis for a subject. These methods comprise analyzing a test sample obtained from the subject according to the methods described herein to provide a signal that is related to the presence or amount of latent protein C. The results of the analysis, in the form of assay results, are correlated to a diagnosis, and/or to the likelihood of a future outcome, either positive (e.g., that the subject is likely to live) or negative (e.g., that the subject is at an increased risk of death). Preferred methods are used in ruling in or out a diagnosis selected from the group consisting of SIRS, sepsis, severe sepsis, septic shock and multiple organ dysfunction syndrome, or in the prognosis (risk stratification) of such conditions.

In another related aspect, the invention relates to methods for monitoring the condition of a subject. These methods comprise analyzing a test sample obtained from the subject according to the methods described herein to provide a signal that is related to the presence or amount of latent protein C. The results of the analysis, in the form of assay results, are correlated to the clinical state of the subject. Preferred methods are used to monitor a treatment regimen being delivered to a subject, most preferably where the subject has been diagnosed with a condition selected from the group consisting of SIRS, sepsis, severe sepsis, septic shock and multiple organ dysfunction syndrome.

In yet a further aspect, the invention relates to devices to perform one or more of the methods described herein. In the case of a device for performing a sandwich immunoassay, the devices preferably contain a diagnostic zone comprising a first antibody bound thereto that binds latent protein C, and a second device zone comprising a second antibody conjugated to a signal development element, wherein one or both of the first and second antibodies are sensitive for, or specifically bind, latent protein C relative to activated protein C. In the case of a device for performing a sandwich immunoassay, the devices preferably contain a diagnostic zone comprising latent protein C bound thereto and a second device zone comprising an antibody conjugated to a signal development element; or a diagnostic zone comprising an antibody conjugated to a solid phase, and a second device zone comprising latent protein C conjugated to a signal development element.

Such devices preferably contain a plurality of diagnostic zones, each of which is related to a particular marker of interest. Such devices may be referred to as "arrays" or "microarrays." Following reaction of a sample with the devices, a signal is generated from the diagnostic zone(s), which may then be correlated to the presence or amount of the markers of interest. Numerous suitable devices are known to those of skill in the art, and exemplary devices are described hereinafter.

The invention further provides antibodies that can be used in the above methods or devices. Some antibodies compete with a monoclonal antibody comprising a heavy chain variable region of SEQ ID NO:4 and a light chain variable region of SEQ ID NO:5, or a monoclonal antibody comprising a heavy chain variable region of SEQ ID NO:6 and a light chain variable region of SEQ ID NO:7.

Some antibodies are monoclonal antibodies comprising a heavy chain variable region having at least 90% sequence identity to SEQ ID NO:4 and a light chain variable region having at least 90% sequence identity to SEQ ID NO:5. Some antibodies are monoclonal antibodies comprising a heavy chain variable region having at least 90% sequence identity to SEQ ID NO:6 and a light chain variable region having at least 90% sequence identity to SEQ ID NO:7.

Some antibodies are monoclonal antibodies comprising a heavy chain variable region of SEQ ID NO:4 and a light chain variable region of SEQ ID NO:5. Some antibodies are monoclonal antibodies comprising a heavy chain variable region of SEQ ID NO:6 and a light chain variable region of SEQ ID NO:7. Humanized, chimeric or veneered version of any of these monoclonal antibodies are also provided. Some antibodies are monoclonal antibodies comprising a heavy chain variable region comprising the three CDR regions from SEQ ID NO:4 and a light chain variable region comprising the three CDR regions from SEQ ID NO:5. Some antibodies are monoclonal antibodies comprising a heavy chain variable region comprising the three CDR regions from SEQ ID NO:6 and a light chain variable region comprising the three CDR regions from SEQ ID NO:7. Some antibodies specifically bind to the same epitope as an antibody comprising a heavy chain variable region of SEQ ID NO:4 and a light chain variable region of SEQ ID NO:5. Some antibodies specifically bind to the same epitope as an antibody comprising a heavy chain variable region of SEQ ID NO:6 and a light chain variable region of SEQ ID NO:7.

Binding of the above-described antibodies to latent protein C is preferably not $Ca^{++}$ sensitive. Further, such antibodies preferably specifically bind to latent protein C without specifically binding to active protein C.

DEFINITIONS

Figure 1:
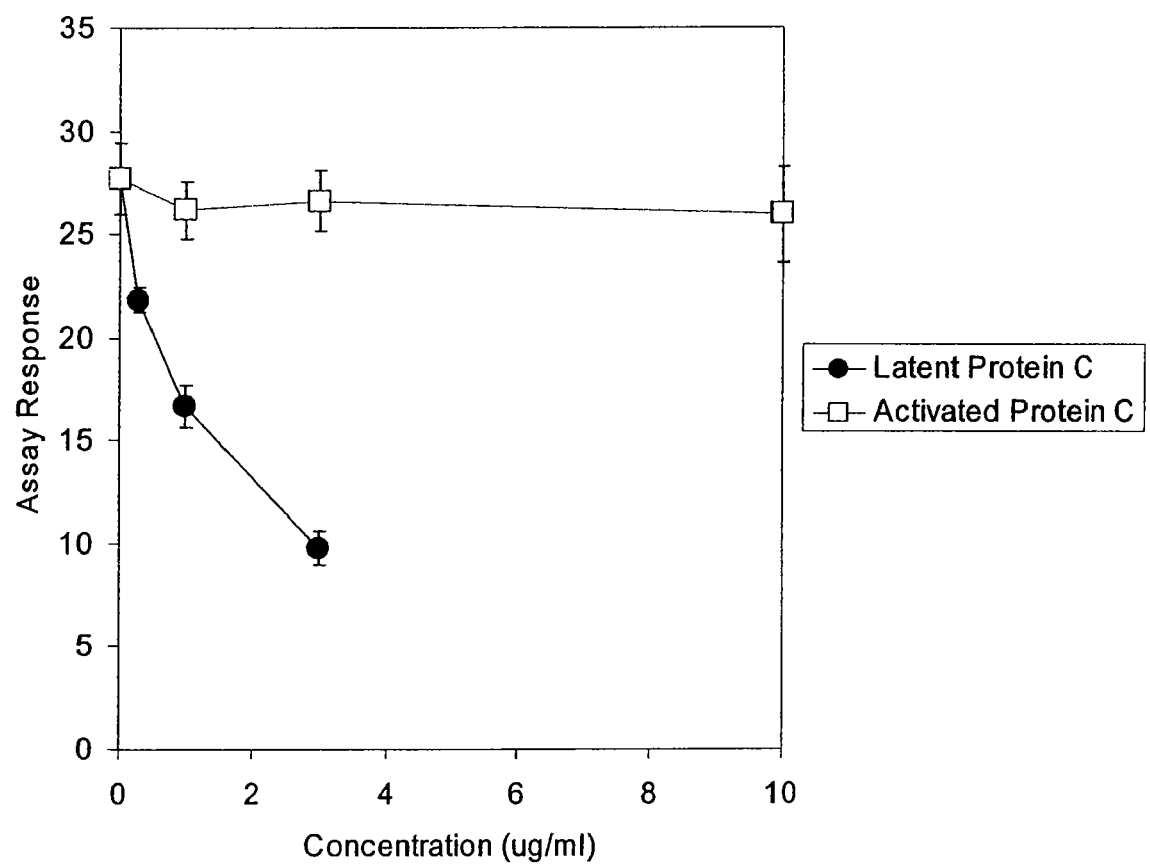
FIG. 1 shows a comparative immunoassay response in an assay of the invention for latent protein C and active protein C.

The term "sepsis" has been used to describe a variety of clinical conditions related to systemic manifestations of inflammation accompanied by an infection. Because of clinical similarities to inflammatory responses secondary to non-infectious etiologies, identifying sepsis has been a particularly challenging diagnostic problem. Recently, the American College of Chest Physicians and the American Society of Critical Care Medicine (Bone et al., *Chest* 101: 1644-53, 1992) published definitions for "Systemic Inflammatory Response Syndrome" (or "SIRS"), which refers generally to a severe systemic response to an infectious or non-infectious insult, and for the related syndromes "sepsis," "severe sepsis," and "septic shock," and extending to multiple organ dysfunction syndrome ("MODS"). These definitions, described below, are intended for each of these phrases for the purposes of the present application.

"SIRS" refers to a condition that exhibits two or more of the following: a temperature >38° C. or <36° C.; a heart rate of >90 beats per minute (tachycardia); a respiratory rate of >20 breaths per minute (tachypnea) or a $P_aCO_2$<4.3 kPa; and a white blood cell count >12,000 per $mm^3$, <4,000 per $mm^3$, or >10% immature (band) forms.

"Sepsis" refers to SIRS, further accompanied by a clinically evident or microbiologically confirmed infection. This infection may be bacterial, fungal, parasitic, or viral.

"Severe sepsis" refers to sepsis, further accompanied by organ hypoperfusion made evident by at least one sign of organ dysfunction such as hypoxemia, oliguria, metabolic acidosis, or altered cerebral function.

"Septic shock" refers to severe sepsis, further accompanied by hypotension, made evident by a systolic blood pressure <90 mm Hg, or the requirement for pharmaceutical intervention to maintain blood pressure.

MODS (multiple organ dysfunction syndrome) is the presence of altered organ function in a patient who is acutely ill such that homeostasis cannot be maintained without intervention. Primary MODS is the direct result of a well-defined insult in which organ dysfunction occurs early and can be directly attributable to the insult itself. Secondary MODS develops as a consequence of a host response and is identified within the context of SIRS.

SEQ ID NO:1 provided a full-length amino acid sequence of human protein C precursor. The first 42 amino acids are a signal peptide. The remaining protein, i.e., residues 53-461 include a light chain and a heavy chain and an intervening peptide. The remaining protein is processed by proteolytic removal of a dipeptide residues 198 and 199 to generate a light chain of residues 43-197 and a heavy chain residues 212 to 461 joined to an activation peptide, residues 200-211. The activation peptide is in turn cleaved by thrombin/thrombomodulin from the heavy chain, leaving a two-chain active protein C. As used herein, the term "latent protein C" refers to one or more polypeptides present in a biological sample that are derived from the protein C precursor and that contain the protein C activation peptide and thrombin cleavage site, together with at least some additional heavy chain residues. Preferred latent protein C molecules contain both heavy chain and light chain residues, and more preferably contain at least 90% of the heavy and light chain residues present in full length latent protein C represented by residues 43-461 of the following sequence from Swiss-Prot P04070 (SEQ ID NO: 1). Some latent C protein molecules contain residues 43-461 of SEQ ID NO:1 or an allelic variant thereof, or residues 43-197 (light chain) and 200-461 (inactive heavy chain) of SEQ ID NO:1 or an allelic variant thereof. The term "active protein C" refers to one or more polypeptides present in a biological sample that are derived from the protein C precursor and that lack the protein C activation peptide and thrombin cleavage site, but contain at least some other heavy chain residues. Preferred active protein C molecules contain both heavy chain and light chain residues, and more preferably contain at least 90% of the heavy and light chain residues present in full length active protein C represented by residues 43-197 and 212-461 of the following sequence from Swiss-Prot P04070 (SEQ ID NO: 1). Some active protein molecules contain residues 43-197 and 212-461 of SEQ ID NO:1 or an allelic variant of this sequence.

```
SEQ ID NO: 1:
         10         20         30         40
MWQLTSLLLF VATWGISGTP APLDSVFSSS ERAHQVLRIR 50         60         70         80
KRANSFLEEL RHSSLERECI EEICDFEEAK EIFQNVDDTL 90        100        110        120
AFWSKHVDGD QCLVLPLEHP CASLCCGHGT CIDGIGSFSC 130        140        150        160
DCRSGWEGRF CQREVSFLNC SLDNGGCTHY CLEEVGWRRC 170        180        190        200
SCAPGYKLGD DLLQCHPAVK FPCGRPWKRM EKKRSNLKRD 210        220        230        240
TEDQEDQVDP RLIDGKMTRR GDSPWQVVLL DSKKKLACGA 250        260        270        280
VLIHPSWVLT AAHCMDESKK LLVRLGEYDL RRWEKWELDI 290        300        310        320
DIKEVFVHPN YSKSTTDNDI ALLHLAQPAT LSQTIVPICL 330        340        350        360
PDSGLAEREL NQAGQETLVT GWGYHSSREK EAKRNRTFVL 370        380        390        400
NFIKIPVVPH NECSEVMSNM VSENMLCAGI LGDRQDACEG 410        420        430        440
DSGGPMVASF HGTWFLVGLV SWGEGCGLLH NYGVYTKVSR 450        460
YLDWIHGHIR DKEAPQKSWA P
```

Preferred assays are "configured to detect" a particular marker. As the term is used herein, an assay is "configured to detect" a marker if an assay can generate a detectable signal indicative of the presence or amount of a physiologically relevant concentration of a particular polypeptide or set of polypeptides of interest. In preferred embodiments, the assays of the present invention are configured to generate a detectable signal when latent protein C is present at a concentration selected from 1 µg/mL to 5 µg/mL, preferably when measured in a blood, serum, and/or plasma sample. In other preferred embodiments, the assays of the present invention are configured including selection of antibodies to generate a detectable signal when full length latent protein C represented by residues 43-461 of Swiss-Prot P04070 is present at a concentration selected from 1 µg/mL to 5 µg/mL. The protein C can be measured in a blood, serum, and/or plasma sample. This is not intended to indicate that such assays do not generate a detectable signal outside of this recited concentration range; only that at some concentration within this concentration range the assay does generate a detectable signal.

Such assays may also be configured to be "sensitive" to loss of a particular epitope, e.g., the loss of residues from protein C upon cleavage by thrombin/thrombomodulin. As the term is used herein, an assay is "sensitive" for a first polypeptide or set of polypeptides (referred to herein as an "intended target molecule") relative to a second polypeptide or set of polypeptides (referred to herein as an "non-target molecule") if an assay signal indicative of the presence or amount of a physiologically relevant concentration of the target molecule is about 5-fold greater than a signal obtained from an equimolar amount of the non-target molecule. Preferably the assay signal will be at least about 5 fold, preferably 10 fold, more preferably 25-fold, even more preferably 50-fold, and most preferably 100-fold or more than a signal obtained from an equimolar amount of the non-target molecule, most preferably when measured in a blood, serum, and/or plasma sample. In preferred embodiments, the intended target molecule is latent protein C, and the non-target molecule is active protein C. In particularly preferred embodiments, the assay signal obtained from 3 µg/mL of latent protein C will be at least about 5 fold, preferably 10 fold, more preferably 25-fold, even more preferably 50-fold, and most preferably 100-fold or more as compared to a signal obtained from an equimolar amount of active protein C, preferably when measured in a blood, serum, and/or plasma sample. In other particularly preferred embodiments, the assay signal obtained from full length latent protein C represented by residues 43-461 of Swiss-Prot P04070 will be at least about 5 fold, preferably 10 fold, more preferably 25-fold, even more preferably 50-fold, and most preferably 100-fold or more for 3 µg/mL or more as compared to a signal obtained from an equimolar amount of active protein C, preferably when measured in a blood, serum, and/or plasma sample. This is not intended to indicate that such assays do not generate a detectable signal from latent protein C having a different sequence (for example, a truncated form of latent protein C); only that latent protein C having this particular sequence does generate an appropriate detectable signal.

The methods described hereinafter may combine a latent protein C assay with assay(s) for one or more other markers that are derived from the subject. The term "subject-derived marker" as used herein refers to protein, polypeptide, phospholipid, nucleic acid, prion, glycoprotein, proteoglycan, glycolipid, lipid, lipoprotein, carbohydrate, or small molecule markers that are expressed or produced by one or more cells of the subject. The presence, absence, amount, or change in amount of one or more markers may indicate that a particular disease is present, or may indicate that a particular disease is absent. Additional markers may be used that are derived not from the subject, but rather that are expressed by pathogenic or infectious organisms that are correlated with a particular disease. Such markers are preferably protein, polypeptide, phospholipid, nucleic acid, prion, or small molecule markers that identify the infectious diseases described above.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine, saliva, sputum, and pleural effusions. Some test samples are more readily analyzed following a fractionation or purification procedure, for example, separation of whole blood into serum or plasma components. Thus, a test sample is preferably blood or one of its fractions, most preferably serum or plasma.

Generally the signals obtained from the assays herein are either directly related to the presence or the amount of the analyte of interest. In the case of a sandwich immunoassay for example, the amount of signal obtained is a direct result of sandwich complexes formed between the labeled species (e.g., antibody), the analyte, and the solid phase species (e.g., antibody), and are performed under conditions where the signal depends on the amount of analyte present in the sample. In the case of a competitive immunoassay, the amount of signal obtained is inversely related to the amount of analyte present in the sample, as the analyte competes for binding to a limited amount of binding species (e.g., antibody). The term "relating a signal to the presence or amount of an analyte" as that term is used herein reflects this understanding. Assay signals are typically related to the presence or amount of an analyte through the use of a standard curve calculated using known concentrations of the analyte of interest.

As used herein, a "plurality" refers to at least two. Preferably, a plurality refers to at least 3, more preferably at least 5, even more preferably at least 10, even more preferably at least 15, and most preferably at least 20. In particularly preferred embodiments, a plurality is a large number, i.e., at least 100.

The term "subject" as used herein refers to a human or non-human organism. Thus, the methods and compositions described herein are applicable to both human and veterinary disease. Further, although a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, amount, or change in amount of which is indicative of the presence, severity, or absence of the condition. In the case of the present invention, "diagnosis" can include using the results of a latent protein C assay of the present invention, optionally together with other clinical characteristics, to arrive at a final diagnosis or a differential diagnosis for the subject from which a sample was obtained and assayed.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing mortality in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient. In the case of the present invention, "prognosis" can include using the results of a latent protein C assay of the present invention, optionally together with other clinical characteristics, to arrive at a prognosis for the subject from which a sample was obtained and assayed.

The term "correlating," as used herein in reference to the use of markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels are correlated to a global probability or a particular outcome, for example using Receiver Operating Characteristic (ROC) analysis.

Measures of test accuracy may be obtained as described in Fischer et al., *Intensive Care Med.* 29: 1043-51, 2003, and used to determine the effectiveness of a given marker (e.g., latent protein C) or panel of markers. These measures include sensitivity and specificity, predictive values, likelihood ratios, diagnostic odds ratios, and receiver operating characteristic (ROC) curve areas. As discussed above, suitable tests may exhibit one or more of the following results on these various measures: at least 75% sensitivity, combined with at least 75% specificity; ROC curve area of at least 0.6, more preferably 0.7, still more preferably at least 0.8, even more preferably at least 0.9, and most preferably at least 0.95; and/or a positive likelihood ratio (calculated as sensitivity/(1-specificity)) of at least 5, more preferably at least 10, and most preferably at least 20, and a negative likelihood ratio (calculated as (1-sensitivity)/specificity) of less than or equal to 0.3, more preferably less than or equal to 0.2, and most preferably less than or equal to 0.1.

The term "discrete" as used herein refers to areas of a surface that are non-contiguous. That is, two areas are discrete from one another if a border that is not part of either area completely surrounds each of the two areas.

The term "independently addressable" as used herein refers to discrete areas of a surface from which a specific signal may be obtained.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

The term "specifically binds" is not intended to indicate that an antibody binds exclusively to its intended target. Rather, an antibody "specifically binds" if its affinity for its intended target is about 5-fold greater when compared to its affinity for a specified non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ M$^{-1}$. Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$. In preferred embodiments, the intended target molecule is latent protein C, and the specified non-target molecule is active protein C. Specific binding between an antibody and latent protein C thus refers to the ability of the antibody to preferentially bind to the latent protein C relative to active protein C. An antibody specifically binding to latent protein C preferably shows no detectable signal from binding to active protein C at a concentration of active protein C of up to 7 µg/ml under assay conditions described in any of the Examples of the application.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1 \times 10^{-6}$ moles/liter, is more preferably at least about $1 \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "therapy regimen" refers to one or more interventions made by a caregiver in hopes of treating a disease or condition. A preferred therapy regimen for the treatment of sepsis is administration of recombinantly produced human activated protein C (drotrecogin alfa, or XIGRIS® (Eli Lilly)). The term "early sepsis therapy regimen" refers to a set of supportive therapies designed to reduce the risk of mortality when administered within the initial 24 hours, more preferably within the initial 12 hours, and most preferably within the initial 6 hours or earlier, of assigning a diagnosis of SIRS, sepsis, severe sepsis, septic shock, or MODS to a subject. Such supportive therapies comprise a spectrum of treatments including resuscitation, fluid delivery, vasopressor administration, inotrope administration, steroid administration, blood product administration, and/or sedation. See, e.g., Dellinger et al., *Crit. Care Med.* 32: 858-873, 2004, and Rivers et al., *N. Engl. J. Med.* 345: 1368-1377, 2001 (providing a description of "early goal directed therapy" as that term is used herein), each of which is hereby incorporated by reference. Preferably, such an early sepsis therapy regimen comprises one or more, and preferably a plurality, of the following therapies: a. maintenance of a central venous pressure of 8-12 mm Hg, preferably by administration of crystalloids and/or colloids as necessary; b. maintenance of a mean arterial pressure of ≧65 mm Hg, preferably by administration of vasopressors and/or vasodilators as necessary; c. maintenance of a central venous oxygen saturation of ≧70%, preferably by administration of transfused red blood cells to a hematocrit of at least 30% and/or administration of dobutamine as necessary; and d. administration of mechanical ventilation as necessary.

The term "marker" as used herein refers to proteins, polypeptides, glycoproteins, proteoglycans, lipids, lipoproteins, glycolipids, phospholipids, nucleic acids, carbohydrates, etc. or small molecules to be used as targets for screening test samples obtained from subjects. "Proteins or polypeptides" used as markers in the present invention are contemplated to include any fragments thereof, in particular, immunologically detectable fragments. Markers can also include clinical "scores" such as a pre-test probability assignment, a pulmonary hypertension "Daniel" score, an NIH stroke score, a Sepsis Score of Elebute and Stoner, a Duke Criteria for Infective Endocarditis, a Mannheim Peritonitis Index, an "Apache" score, etc.

The term "related marker" as used herein refers to one or more fragments of a particular marker or its biosynthetic parent that may be detected as a surrogate for the marker itself or as independent markers. For example, human BNP is derived by proteolysis of a 108 amino acid precursor molecule, referred to hereinafter as $BNP_{1-108}$. Mature BNP, or "the BNP natriuretic peptide," or "BNP-32" is a 32 amino acid molecule representing amino acids 77-108 of this precursor, which may be referred to as $BNP_{77-108}$. The remaining residues 1-76 are referred to hereinafter as $BNP_{1-76}$, and are also known as "NT-proBNP." Additionally, related markers may be the result of covalent modification of the parent marker, for example by oxidation of methionine residues, ubiquitination, cysteinylation, nitrosylation (e.g., containing nitrotyrosine residues), halogenation (e.g., containing chlorotyrosine and/or bromotyrosine residues), glycosylation, complex formation, differential splicing, etc.

The sequence of the 108 amino acid BNP precursor pro-BNP ($BNP_{1-108}$) is as follows, with mature BNP ($BNP_{77-108}$) underlined:

```
HPLGSPGSAS DLETSGLQEQ RNHLQGKLSE LQVEQTSLEP LQESPRPTGV   50 (SEQ ID NO: 2)
WKSREVATEG IRGHRKMVLY TLRAPRSPKM VQGSGCFGRK MDRISSSSGL  100
GCKVLRRH.                                              108
```

$BNP_{1-108}$ is synthesized as a larger precursor pre-pro-BNP having the following sequence (with the "pre" sequence shown in bold):

```
MDPQTAPSRA LLLLLFLHLA FLGGRSHPLG SPGSASDLET SGLQEQRNHL   50 (SEQ ID NO: 3)
QGKLSELQVE QTSLEPLQES PRPTGVWKSR EVATEGIRGH RKMVLYTLRA  100
PRSPKMVQGS GCFGRKMDRI SSSSGLGCKV LRRH.                 134
```

Although mature BNP itself may be used as a marker in the present invention, the prepro-BNP, $BNP_{1-108}$ and $BNP_{1-76}$ molecules represent BNP-related markers that may be measured either as surrogates for mature BNP or as markers in and of themselves. In addition, one or more fragments of these molecules, including BNP-related polypeptides selected from the group consisting of $BNP_{77-106}$, $BNP_{79-106}$, $BNP_{76-107}$, $BNP_{69-108}$, $BNP_{79-108}$, $BNP_{80-108}$, $BNP_{81-108}$, $BNP_{83-108}$, $BNP_{39-86}$, $BNP_{53-85}$, $BNP_{66-98}$, $BNP_{30-103}$, $BNP_{11-107}$, $BNP_{9-106}$, and $BNP_{3-108}$ may also be present in circulation. In addition, natriuretic peptide fragments, including BNP fragments, may comprise one or more oxidizable methionines, the oxidation of which to methionine sulfoxide or methionine sulfone produces additional BNP-related markers. See, e.g., U.S. patent Ser. No. 10/419,059, filed Apr. 17, 2003, which is hereby incorporated by reference in its entirety including all tables, figures and claims.

Because production of marker fragments is an ongoing process that may be a function of, inter alia, the elapsed time between onset of an event triggering marker release into the tissues and the time the sample is obtained or analyzed; the elapsed time between sample acquisition and the time the sample is analyzed; the type of tissue sample at issue; the storage conditions; the quantity of proteolytic enzymes present; etc., it may be necessary to consider this degradation when both designing an assay for one or more markers, and when performing such an assay, in order to provide an accurate prognostic or diagnostic result. In addition, individual antibodies that distinguish amongst a plurality of marker fragments may be individually employed to separately detect the presence or amount of different fragments. The results of this individual detection may provide a more accurate prognostic or diagnostic result than detecting the plurality of fragments in a single assay. For example, different weighting factors may be applied to the various fragment measurements to provide a more accurate estimate of the amount of natriuretic peptide originally present in the sample.

In a similar fashion, many of the markers described herein are synthesized as larger precursor molecules, which are then processed to provide mature marker; and/or are present in circulation in the form of fragments of the marker. Thus, "related markers" to each of the markers described herein may be identified and used in an analogous fashion to that described above for BNP.

Removal of polypeptide markers from the circulation often involves degradation pathways. Moreover, inhibitors of such degradation pathways may hold promise in treatment of certain diseases. See, e.g., Trindade and Rouleau, *Heart Fail. Monit.* 2: 2-7, 2001. However, the measurement of the polypeptide markers has focused generally upon measurement of the intact form without consideration of the degradation state of the molecules. Assays may be designed with an understanding of the degradation pathways of the polypeptide markers and the products formed during this degradation, in order to accurately measure the biologically active forms of a particular polypeptide marker in a sample. The unintended measurement of both the biologically active polypeptide marker(s) of interest and inactive fragments derived from the markers may result in an overestimation of the concentration of biologically active form(s) in a sample.

The failure to consider the degradation fragments that may be present in a clinical sample may have serious consequences for the accuracy of any diagnostic or prognostic method. Consider for example a simple case, where a sandwich immunoassay is provided for BNP, and a significant amount (e.g., 50%) of the biologically active BNP that had been present has now been degraded into an inactive form. An immunoassay formulated with antibodies that bind a region common to the biologically active BNP and the inactive fragment(s) will overestimate the amount of biologically active BNP present in the sample by 2-fold, potentially resulting in a "false positive" result. Overestimation of the biologically active form(s) present in a sample may also have serious consequences for patient management. Considering the BNP example again, the BNP concentration may be used to determine if therapy is effective (e.g., by monitoring BNP to see if an elevated level is returning to normal upon treatment). The same "false positive" BNP result discussed above may lead the physician to continue, increase, or modify treatment because of the false impression that current therapy is ineffective.

Likewise, it may be necessary to consider the complex state of one or more markers described herein. For example, troponin exists in muscle mainly as a "ternary complex" comprising three troponin polypeptides (T, I and C). But troponin I and troponin T circulate in the blood in forms other than the I/T/C ternary complex. Rather, each of (i) free cardiac-specific troponin I, (ii) binary complexes (e.g., troponin I/C complex), and (iii) ternary complexes all circulate in the blood. Furthermore, the "complex state" of troponin I and T may change over time in a patient, e.g., due to binding of free troponin polypeptides to other circulating troponin polypeptides. Immunoassays that fail to consider the "complex state" of troponin may not detect all of the cardiac-specific isoform of interest.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest, U.S. Department of Health and Human Services, 1983, 1987. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

For other sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. One example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi. nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89, 10915 (1989)).

The terms "isolated" or "purified" means that an object species (e.g., an antibody) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species.

DETAILED DESCRIPTION OF THE INVENTION

The present invention relates to methods and compositions for the measurement of latent protein C in patient samples, such as blood samples, or blood fractions such as serum or plasma. Such methods and compositions may be used in symptom-based differential diagnosis and/or prognosis, and selection of treatment regimens and/or monitoring of subjects. The subjects to be monitored include those believed to suffer from, or diagnosed as suffering from a systemic inflammatory response syndrome (SIRS). The invention provides monoclonal antibodies in isolated form that specifically bind to latent protein C and lack binding to APC. These monoclonal antibodies to be used in methods of diagnosis and/or prognosis. Preferred antibodies are not calcium sensitive and compete with monoclonal antibody Z1XM01701 and/or Z3XM01011 for binding to latent protein C.

I. SIRS/Sepsis

Sepsis refers to SIRS, further accompanied by a clinically evident or microbiologically confirmed infection. This infection may be bacterial, fungal, parasitic, or viral. However, 50% or more of patients exhibiting strong clinical evidence of sepsis are negative on culture. Almost all patients with severe sepsis have a generalized host response to infection that includes increased coagulation activation reduced anticoagulation, impaired fibrinolysis, endothelial injury and inflammatory activity.

A systemic inflammatory response leading to a diagnosis of SIRS may be related to both infection and to numerous non-infective etiologies, including burns, pancreatitis, trauma, heat stroke, and neoplasia. Although conceptually it may be relatively simple to distinguish between sepsis and non-septic SIRS, no diagnostic tools have been described to unambiguously distinguish these related conditions. See, e.g., Llewelyn and Cohen, *Int. Care Med.* 27: S10-S32, 2001. For example, because more than 90% of sepsis cases involve bacterial infection, the "gold standard" for confirming infection has been microbial growth from blood, urine, pleural fluid, cerebrospinal fluid, peritoneal fluid, synovial fluid, sputum, or other tissue specimens. Such culture has been reported, however, to fail to confirm 50% or more of patients exhibiting strong clinical evidence of sepsis. See, e.g., Jaimes et al., *Int. Care Med* 29: 1368-71, published electronically Jun. 26, 2003.

The physiologic responses leading to the systemic manifestations of inflammation in sepsis remain unclear. Activation of immune cells occurs in response to the LPS endotoxin of gram negative bacteria and exotoxins of gram positive bacteria. This activation leads to a cascade of events mediated by proinflammatory cytokines, adhesion molecules, vasoactive mediators, and reactive oxygen species. Various organs, including the liver, lungs, heart, and kidney are affected directly or indirectly by this cascade. Sepsis is also associated with disseminated intravascular coagulation ("DIC"), mediated presumably by cytokine activation of coagulation. Fluid and electrolyte balance are also affected by increases in capillary perfusion and reduced oxygenation of tissues. Unchecked, the uncontrolled inflammatory response created can lead to ischemia, loss of organ function, and death.

Despite the availability of antibiotics and supportive therapy, sepsis represents a significant cause of morbidity and mortality. A recent study estimated that 751,000 cases of severe sepsis occur in the United States annually, with a mortality rate of from 30-50%. Angus et al., *Crit. Care Med.* 29: 1303-10, 2001. Recently, an organization of medical care groups referred to as the "Surviving Sepsis Campaign" issued guidelines for managing subjects suffering from severe sepsis and septic shock. Dellinger et al., *Crit. Care Med.* 32: 858-873, 2004. These guidelines draw from, amongst other sources, the "Early Goal Directed Therapy" therapy regimen developed by Rivers and colleagues. See, e.g., *New Engl. J. Med.* 345: 1368-77. 2001.

Several laboratory tests have been investigated or proposed for use, in conjunction with a complete clinical examination of a subject, for the diagnosis and prognosis of sepsis. See, e.g., U.S. Pat. Nos. 5,639,617 and 6,303,321; Patent publications US2005/0196817, WO2005/048823, WO2004/046181, WO2004/043236, US2005/0164238; and Charpentier et al., *Crit. Care Med.* 32: 660-65, 2004; Castillo et al., *Int. J. Infect. Dis.* 8: 271-74, 2004; Chua and Kang-Hoe, *Crit. Care* 8: R248-R250, 2004; Witthaut et al., *Int. Care Med.* 29: 1696-1702, 2003; Jones and Kline, *Ann. Int. Med.* 42: 714-15, 2003; Maeder et al., *Swiss Med. Wkly.* 133: 515-18, 2003; Giamarellos-Bourboulis et al., *Intensive Care Med.* 28: 1351-56, 2002; Harbarth et al., *Am. J. Respir. Crit. Care Med.* 164: 396-402, 2001; Martin et al., *Pediatrics* 108: 2001; and Bossink et al., *Chest* 113: 1533-41, 1998.

Active protein C has been reported to be a prognostic indicator in patients with sepsis and/or SIRS. Decreased protein C levels have been linked to mortality in both sepsis and septic shock. It has been theorized that during sepsis, in addition to the absolute reductions in protein C levels, there is a reduction in the conversion of protein C to its active form due to the down-regulation of thrombomodulin by inflammatory cytokines. Thrombomodulin coupled to thrombin is involved in the activation of protein C in vivo. Activated protein C is believed to have antithrombotic, profibrinolytic, and anti-inflammatory effects. Active protein C (APC) has been shown to be an important prognostic indicator in patients with sepsis, presumably by virtue of its ability to down-regulate coagulation as well as inflammation.

The present methods identify the amount of latent protein C in the blood of patients having or suspected of having SIRS and/or sepsis. The present application shows that reduced levels of latent C are associated with these conditions. This result is surprising in view of the theory that reduced levels of active protein C result at least in part from decreased activation of latent protein C. The level of latent protein C can be used as a prognostic, diagnostic and selection of treatment regimens for sepsis. This assay is particularly useful in patients that are already undergoing treatment with APC therapeutics because the administered APC does not affect the result, as it would if APC were detected.

II. Identification of Marker Panels

In accordance with the present invention, there are provided methods and systems for the identification of one or more markers that may be combined with the latent protein C assays described herein for diagnosis, prognosis, and/or the determination of an appropriate therapeutic course. Suitable methods for identifying markers useful for such purposes are described in detail in U.S. Provisional Patent Application No. 60/436,392 filed Dec. 24, 2002, PCT application US03/41426 filed Dec. 23, 2003, U.S. patent application Ser. No. 10/331,127 filed Dec. 27, 2002, and PCT application No. US03/41453, each of which is hereby incorporated by reference in its entirety, including all tables, figures, and claims. One skilled in the art will also recognize that univariate analysis of markers can be performed and the data from the univariate analyses of multiple markers can be combined to form panels of markers to differentiate different disease conditions. Such methods include multiple linear regression, determining interaction terms, stepwise regression, etc.

To allow a determination of test accuracy, a "gold standard" test criterion may be selected which allows selection of subjects into two or more groups for comparison by the foregoing methods. In the case of sepsis, this gold standard may be recovery of organisms from culture of blood, urine, pleural fluid, cerebrospinal fluid, peritoneal fluid, synovial fluid, sputum, or other tissue specimens. This implies that those negative for the gold standard are free of sepsis; however, as discussed above, 50% or more of patients exhibiting strong clinical evidence of sepsis are negative on culture. In this case, those patients showing clinical evidence of sepsis but a negative gold standard result may be omitted from the comparison groups. Alternatively, an initial comparison of confirmed sepsis subjects may be compared to normal healthy control subjects. In the case of a prognosis, mortality is a common test criterion.

A panel consisting of the markers referenced herein and/or their related markers may be constructed to provide relevant information related to the diagnosis of interest. Such a panel may be constructed using 1, 2, 3, 4, 5, 6, 7, 8, 9, 10, 11, 12, 13, 14, 15, 16, 17, 18, 19, 20, or more individual markers. The analysis of a single marker or subsets of markers comprising a larger panel of markers can be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity.

Examples of other markers that can be used to analyze the presence and severity in addition to Protein C include, but are not limited to, Protein S, prothrombin time (PT), activated partial thrombolastin time (APTT), plasminogen activator inhibitor (PAI-1), prothrombin fragment F1.2, ubiquitin/ubiquitinated proteins.

The following table provides a list of additional preferred markers for use in the present invention. Further detail is provided in US2005/0148029, which is hereby incorporated by reference in its entirety. As described herein, markers related to each of these markers are also encompassed by the present invention.

| Marker | Classification |
| --- | --- |
| Myoglobin | Tissue injury |
| E-selectin | Tissue injury |
| VEGF | Tissue injury |
| EG-VEGF | Tissue injury |
| Troponin I and complexes | Myocardial injury |
| Troponin T and complexes | Myocardial injury |
| Annexin V | Myocardial injury |
| B-enolase | Myocardial injury |
| CK-MB | Myocardial injury |
| Glycogen phosphorylase-BB | Myocardial injury |
| Heart type fatty acid binding protein | Myocardial injury |
| Phosphoglyceric acid mutase | Myocardial injury |
| S-100ao | Myocardial injury |
| ANP | Blood pressure regulation |
| CNP | Blood pressure regulation |
| Kininogen | Blood pressure regulation |
| CGRP II | Blood pressure regulation |
| urotensin II | Blood pressure regulation |
| BNP | Blood pressure regulation |
| NT-proBNP | Blood pressure regulation |
| proBNP | Blood pressure regulation |
| calcitonin gene related peptide | Blood pressure regulation |
| arg-Vasopressin | Blood pressure regulation |
| Endothelin-1 (and/or Big ET-1) | Blood pressure regulation |
| Endothelin-2 (and/or Big ET-2) | Blood pressure regulation |
| Endothelin-3 (and/or Big ET-3) | Blood pressure regulation |
| procalcitonin | Blood pressure regulation |
| calcyphosine | Blood pressure regulation |
| adrenomedullin | Blood pressure regulation |
| aldosterone | Blood pressure regulation |
| angiotensin 1 (and/or angiotensinogen 1) | Blood pressure regulation |
| angiotensin 2 (and/or angiotensinogen 2) | Blood pressure regulation |
| angiotensin 3 (and/or angiotensinogen 3) | Blood pressure regulation |
| Bradykinin | Blood pressure regulation |
| Tachykinin-3 | Blood pressure regulation |
| calcitonin | Blood pressure regulation |
| Renin | Blood pressure regulation |
| Urodilatin | Blood pressure regulation |
| Ghrelin | Blood pressure regulation |
| Plasmin | Coagulation and hemostasis |
| Thrombin | Coagulation and hemostasis |
| Antithrombin-III | Coagulation and hemostasis |
| Fibrinogen | Coagulation and hemostasis |
| von Willebrand factor | Coagulation and hemostasis |
| D-dimer | Coagulation and hemostasis |
| PAI-1 | Coagulation and hemostasis |
| Protein C (Total or Active) | Coagulation and hemostasis |
| Soluble Endothelial Protein C Receptor (EPCR) | Coagulation and hemostasis |
| TAFI | Coagulation and hemostasis |
| Fibrinopeptide A | Coagulation and hemostasis |
| Plasmin alpha 2 antiplasmin complex | Coagulation and hemostasis |
| Platelet factor 4 | Coagulation and hemostasis |
| Platelet-derived growth factor | Coagulation and hemostasis |
| P-selectin | Coagulation and hemostasis |
| Prothrombin fragment 1 + 2 | Coagulation and hemostasis |
| B-thromboglobulin | Coagulation and hemostasis |
| Thrombin antithrombin III complex | Coagulation and hemostasis |
| Thrombomodulin | Coagulation and hemostasis |
| Thrombus Precursor Protein | Coagulation and hemostasis |
| Tissue factor | Coagulation and hemostasis |
| Tissue factor pathway inhibitor-α | Coagulation and hemostasis |
| Tissue factor pathway inhibitor-β | Coagulation and hemostasis |
| basic calponin 1 | Vascular tissue |
| beta like 1 integrin | Vascular tissue |
| Calponin | Vascular tissue |
| CSRP2 | Vascular tissue |
| elastin | Vascular tissue |
| Endothelial cell-selective adhesion molecule (ESAM) | Vascular tissue |
| Fibrillin 1 | Vascular tissue |
| Junction Adhesion Molecule-2 | Vascular tissue |
| LTBP4 | Vascular tissue |

-continued

| Marker | Classification |
| --- | --- |
| smooth muscle myosin | Vascular tissue |
| transgelin | Vascular tissue |
| Carboxyterminal propeptide of type I procollagen (PICP) | Collagen synthesis |
| Collagen carboxyterminal telopeptide (ICTP) | Collagen degradation |
| APRIL (TNF ligand superfamily member 13) | Inflammatory |
| CD27 (TNFRSF7) | Inflammatory |
| Complement C3a | Inflammatory |
| CCL-5 (RANTES) | Inflammatory |
| CCL-8 (MCP-2) | Inflammatory |
| CCL-16 | Inflammatory |
| CCL-19 (macrophage inflammatory protein-3β) | Inflammatory |
| CCL-20 (MIP-3α) | Inflammatory |
| CCL-23 (MIP-3) | Inflammatory |
| CXCL-5 (small inducible cytokine B5) | Inflammatory |
| CXCL-9 (small inducible cytokine B9) | Inflammatory |
| CXCL-13 (small inducible cytokine B13) | Inflammatory |
| CXCL-16 (small inducible cytokine B16) | Inflammatory |
| DPP-II (dipeptidyl peptidase II) | Inflammatory |
| DPP-IV (dipeptidyl peptidase IV) | Inflammatory |
| Glutathione S Transferase | Inflammatory |
| HIF 1 ALPHA | Inflammatory |
| IL-25 | Inflammatory |
| IL-23 | Inflammatory |
| IL-22 | Inflammatory |
| IL-18 | Inflammatory |
| IL-13 | Inflammatory |
| IL-12 | Inflammatory |
| IL-10 | Inflammatory |
| IL-1-Beta | Inflammatory |
| IL-1ra | Inflammatory |
| IL-4 | Inflammatory |
| IL-6 | Inflammatory |
| IL-8 | Inflammatory |
| Lysophosphatidic acid | Inflammatory |
| MDA-modified LDL | Inflammatory |
| Human neutrophil elastase | Inflammatory |
| C-reactive protein | Inflammatory |
| Insulin-like growth factor | Inflammatory |
| Inducible nitric oxide synthase | Inflammatory |
| Intracellular adhesion molecule | Inflammatory |
| Lipocalin-2 | Inflammatory |
| Lactate dehydrogenase | Inflammatory |
| MCP-1 | Inflammatory |
| MMP-1 | Inflammatory |
| MMP-2 | Inflammatory |
| MMP-3 | Inflammatory |
| MMP-7 | Inflammatory |
| MMP-9 | Inflammatory |
| TIMP-1 | Inflammatory |
| TIMP-2 | Inflammatory |
| TIMP-3 | Inflammatory |
| n-acetyl aspartate | Inflammatory |
| PTEN | Inflammatory |
| Phospholipase A2 | Inflammatory |
| TNF Receptor Superfamily Member 1A | Inflammatory |
| TNFRSF3 (lymphotoxin β receptor) | Inflammatory |
| Transforming growth factor beta | Inflammatory |
| TREM-1 | Inflammatory |
| TREM-1sv | Inflammatory |
| TL-1 (TNF ligand related molecule-1) | Inflammatory |
| TL-1a | Inflammatory |
| Tumor necrosis factor alpha | Inflammatory |
| Vascular cell adhesion molecule | Inflammatory |
| Vascular endothelial growth factor | Inflammatory |
| cystatin C | Inflammatory |
| substance P | Inflammatory |
| Myeloperoxidase (MPO) | Inflammatory |
| macrophage inhibitory factor | Inflammatory |
| Fibronectin | Inflammatory |
| cardiotrophin 1 | Inflammatory |
| Haptoglobin | Inflammatory |
| PAPPA | Inflammatory |
| s-CD40 ligand | Inflammatory |
| HMG-1 (or HMGB1) | Inflammatory |

| Marker | Classification |
|---|---|
| IL-2 | Inflammatory |
| IL-4 | Inflammatory |
| IL-11 | Inflammatory |
| IL-13 | Inflammatory |
| IL-18 | Inflammatory |
| Eosinophil cationic protein | Inflammatory |
| Mast cell tryptase | Inflammatory |
| VCAM | Inflammatory |
| sICAM-1 | Inflammatory |
| TNFα | Inflammatory |
| Osteoprotegerin | Inflammatory |
| Prostaglandin D-synthase | Inflammatory |
| Prostaglandin E2 | Inflammatory |
| RANK ligand | Inflammatory |
| RANK (TNFRSF11A) | Inflammatory |
| HSP-60 | Inflammatory |
| Serum Amyloid A | Inflammatory |
| s-iL 18 receptor | Inflammatory |
| S-iL-1 receptor | Inflammatory |
| s-TNF P55 | Inflammatory |
| s-TNF P75 | Inflammatory |
| sTLR-1 (soluble toll-like receptor-1) | Inflammatory |
| sTLR-2 | Inflammatory |
| sTLR-4 | Inflammatory |
| TGF-beta | Inflammatory |
| MMP-11 | Inflammatory |
| Beta NGF | Inflammatory |
| CD44 | Inflammatory |
| EGF | Inflammatory |
| E-selectin | Inflammatory |
| Fibronectin | Inflammatory |
| RAGE | Inflammatory |
| Neutrophil elastase | Pulmonary injury |
| KL-6 | Pulmonary injury |
| LAMP 3 | Pulmonary injury |
| LAMP3 | Pulmonary injury |
| Lung Surfactant protein A | Pulmonary injury |
| Lung Surfactant protein B | Pulmonary injury |
| Lung Surfactant protein C | Pulmonary injury |
| Lung Surfactant protein D | Pulmonary injury |
| phospholipase D | Pulmonary injury |
| PLA2G5 | Pulmonary injury |
| SFTPC | Pulmonary injury |
| MAPK10 | Neural tissue injury |
| KCNK4 | Neural tissue injury |
| KCNK9 | Neural tissue injury |
| KCNQ5 | Neural tissue injury |
| 14-3-3 | Neural tissue injury |
| 4.1B | Neural tissue injury |
| APO E4-1 | Neural tissue injury |
| myelin basic protein | Neural tissue injury |
| Atrophin 1 | Neural tissue injury |
| Brain derived neurotrophic factor | Neural tissue injury |
| Brain fatty acid binding protein | Neural tissue injury |
| Brain tubulin | Neural tissue injury |
| CACNA1A | Neural tissue injury |
| Calbindin D | Neural tissue injury |
| Calbrain | Neural tissue injury |
| Carbonic anhydrase XI | Neural tissue injury |
| CBLN1 | Neural tissue injury |
| Cerebellin 1 | Neural tissue injury |
| Chimerin 1 | Neural tissue injury |
| Chimerin 2 | Neural tissue injury |
| CHN1 | Neural tissue injury |
| CHN2 | Neural tissue injury |
| Ciliary neurotrophic factor | Neural tissue injury |
| CK-BB | Neural tissue injury |
| CRHR1 | Neural tissue injury |
| C-tau | Neural tissue injury |
| DRPLA | Neural tissue injury |
| GFAP | Neural tissue injury |
| GPM6B | Neural tissue injury |
| GPR7 | Neural tissue injury |
| GPR8 | Neural tissue injury |
| GRIN2C | Neural tissue injury |
| GRM7 | Neural tissue injury |
| HAPIP | Neural tissue injury |
| HIP2 | Neural tissue injury |
| LDH | Neural tissue injury |
| Myelin basic protein | Neural tissue injury |
| NCAM | Neural tissue injury |
| NT-3 | Neural tissue injury |
| NDPKA | Neural tissue injury |
| Neural cell adhesion molecule | Neural tissue injury |
| NEUROD2 | Neural tissue injury |
| Neurofilament L | Neural tissue injury |
| Neuroglobin | Neural tissue injury |
| neuromodulin | Neural tissue injury |
| Neuron specific enolase | Neural tissue injury |
| Neuropeptide Y | Neural tissue injury |
| Neurotensin | Neural tissue injury |
| Neurotrophin 1, 2, 3, 4 | Neural tissue injury |
| NRG2 | Neural tissue injury |
| PACE4 | Neural tissue injury |
| phosphoglycerate mutase | Neural tissue injury |
| PKC gamma | Neural tissue injury |
| proteolipid protein | Neural tissue injury |
| PTEN | Neural tissue injury |
| PTPRZ1 | Neural tissue injury |
| RGS9 | Neural tissue injury |
| RNA Binding protein Regulatory Subunit | Neural tissue injury |
| S-100β | Neural tissue injury |
| SCA7 | Neural tissue injury |
| secretagogin | Neural tissue injury |
| SLC1A3 | Neural tissue injury |
| SORL1 | Neural tissue injury |
| SREB3 | Neural tissue injury |
| STAC | Neural tissue injury |
| STX1A | Neural tissue injury |
| STXBP1 | Neural tissue injury |
| Syntaxin | Neural tissue injury |
| thrombomodulin | Neural tissue injury |
| transthyretin | Neural tissue injury |
| adenylate kinase-1 | Neural tissue injury |
| BDNF | Neural tissue injury |
| neurokinin A | Neural tissue injury |
| neurokinin B | Neural tissue injury |
| s-acetyl Glutathione | apoptosis |
| cytochrome C | apoptosis |
| Caspase 3 | apoptosis |
| Cathepsin D | apoptosis |
| α-spectrin | apoptosis |

Examples of other markers that can be used to analyze the presence and severity in addition to Protein C include Protein S, prothrombin time (PT), activated partial thrombolastin time (APTT), plasminogen activator inhibitor (PAI-1), prothrombin fragment F1.2, ubiquitin/ubiquitinated proteins. Ubiquitin-mediated degradation of proteins plays an important role in the control of numerous processes, such as the way in which extracellular materials are incorporated into a cell, the movement of biochemical signals from the cell membrane, and the regulation of cellular functions such as transcriptional on-off switches. The ubiquitin system has been implicated in the immune response and development. Ubiquitin is a 76-amino acid polypeptide that is conjugated to proteins targeted for degradation. The ubiquitin-protein conjugate is recognized by a 26S proteolytic complex that splits ubiquitin from the protein, which is subsequently degraded.

It has been reported that sepsis stimulates protein breakdown in skeletal muscle by a nonlysosomal energy-dependent proteolytic pathway, and because muscle levels of ubiquitin mRNA were also increased, the results were interpreted as indicating that sepsis-induced muscle protein breakdown is caused by upregulated activity of the energy-ubiquitin-dependent proteolytic pathway. The same proteolytic pathway has been implicated in muscle breakdown caused by denervation, fasting, acidosis, cancer, and burn injury. Thus, levels of ubiquitinated proteins generally, or of specific ubiquitin-protein conjugates or fragments thereof, can be measured as additional markers of the invention. See, Tiao et al., *J. Clin. Invest.* 99: 163-168, 1997. Moreover, circulating levels of ubiquitin itself can be a useful marker in the methods described herein. See, e.g., Majetschak et al., *Blood* 101: 1882-90, 2003.

Interestingly, ubiquitination of a protein or protein fragment may convert a non-specific marker into a more specific marker of sepsis. For example, muscle damage can increase the concentration of muscle proteins in circulation. But sepsis, by specifically upregulating the ubiquitination pathway, may result in an increase of ubiquitinated muscle proteins, thus distinguishing non-specific muscle damage from sepsis-induced muscle damage.

The skilled artisan will recognize that an assay for ubiquitin may be designed that recognizes ubiquitin itself, ubiquitin-protein conjugates, or both ubiquitin and ubiquitin-protein conjugates. For example, antibodies used in a sandwich immunoassay may be selected so that both the solid phase antibody and the labeled antibody recognize a portion of ubiquitin that is available for binding in both unconjugated ubiquitin and ubiquitin conjugates. Alternatively, an assay specific for ubiquitin conjugates of the muscle protein troponin can use one antibody (on a solid phase or label) that recognizes ubiquitin, and a second antibody (the other of the solid phase or label) that recognizes troponin.

The present invention contemplates measuring ubiquitin conjugates of any marker described herein and/or their related markers. Preferred ubiquitin-muscle protein conjugates for detection as markers include, but are not limited to, troponin I-ubiquitin, troponin T-ubiquitin, troponin C-ubiquitin, binary and ternary troponin complex-ubiquitin, actin-ubiquitin, myosin-ubiquitin, tropomyosin-ubiquitin, and α-actinin-ubiquitin and ubiquitinated markers related thereto.

In similar fashion, other modifications of the markers described herein, or markers related thereto, can be detected. For example, nitrotyrosine, chlorotyrosine, and/or bromotyrosine may be formed by the action of myeloperoxidase in sepsis. See, e.g., U.S. Pat. No. 6,939,716. Assays for nitrotyrosine, chlorotyrosine, and/or bromotyrosine may be designed that recognize one or more of these individual modified amino acids, one or more markers containing one or more of the modified amino acids, or both modified amino acid(s) and modified marker(s).

III. Assay Strategies

The contemplated assays involve detection of the marker latent protein C alone or in combination with any of the markers described herein and/or markers generally used for identification of sepsis, SIRS, and/or like diseases. The contemplated assays can use any of the antibodies described below. One or more such antibodies can be used depending on the assay format. In general, such assays involve contacting a sample containing or suspected of containing latent protein C with at least one antibody that specifically binds to latent protein C. A signal is then generated indicative of binding of the antibody to latent protein C if present in the sample. The signal can be generated directly from a label on the antibody or indirectly as described in various formats below. The signal is then related to the presence or amount of latent protein C in the sample.

Numerous methods and devices are well known to the skilled artisan for the detection and analysis of the markers. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. Robotic instrumentation including but not limited to Beckman Access, Abbott AxSym, Roche ElecSys, Dade Behring Stratus systems are among the immunoassay analyzers that are capable of performing the immunoassays taught herein.

Preferably the markers are analyzed using an immunoassay, and most preferably a sandwich immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Antibodies or other polypeptides can be immobilized onto a variety of solid supports. Solid phases that can be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip can be prepared by coating the antibody or a plurality of antibodies in an array on solid support. This strip can then be dipped into the test sample and then processed quickly through washes and detection steps to generate a measurable signal, such as a colored spot. Antibodies or other polypeptides can be bound to specific zones of assay devices either by conjugating directly to an assay device surface, or by indirect binding. In an example of the later case, antibodies or other polypeptides can be immobilized on particles or other solid supports, and that solid support immobilized to the device surface. In this context, an antibody or other polypeptide "bound" to a particular surface is intended to indicate either direct or indirect binding to that surface.

Biological assays require methods for detection, and one of the most common methods for quantitation of results is to conjugate an enzyme, fluorophore or other molecule to a protein or nucleic acid that has affinity for one of the components in the biological system being studied. Antibody-enzyme conjugates (primary or secondary antibodies) are among the most common protein-protein conjugates used. Detectable labels can include molecules that are themselves detectable (e.g., fluorescent moieties, electrochemical labels, metal chelates, etc.) as well as molecules that can be indirectly detected by production of a detectable reaction product (e.g., enzymes such as horseradish peroxidase, alkaline phosphatase, etc.) or by a specific binding molecule which itself can be detectable (e.g., biotin, digoxigenin, maltose, oligohistidine, 2,4-dintrobenzene, phenylarsenate, ssDNA, dsDNA, etc.). Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter.

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, whereas pyridyl disulfides react with sulfhydryls to produce mixed disulfides. The pyridyl disulfide product is cleavable. Imidoesters are also very useful for protein-protein cross-links.

Heterobifunctional cross-linkers possess two or more different reactive groups that allow for sequential conjugations with specific groups of proteins, minimizing undesirable polymerization or self-conjugation. Heterobifunctional reagents are also used when modification of amines is problematic. Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups. A variety of heterobifunctional cross-linkers, each combining different attributes for successful conjugation, are commercially available. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

Many factors can be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, whereas intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380-8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

For separate or sequential assay of markers, suitable apparati include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of markers on a single surface. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and certain capillary devices (see, e.g., U.S. Pat. No. 6,019,944). In these embodiments, each discrete surface location can have antibodies to immobilize one or more analyte(s) (e.g., a marker) for detection at each location. Surfaces can alternatively have one or more discrete particles (e.g., microparticles or nanoparticles) immobilized at discrete locations of a surface, and the microparticles can include antibodies to immobilize one analyte (e.g., a marker) for detection.

Preferred assay devices of the present invention will comprise a first antibody conjugated to a solid phase and a second antibody conjugated to a signal development element, wherein one or both of the first and second antibodies are sensitive for, or specifically bind, latent protein C relative to activated protein C. Appropriate antibodies binding to different epitopes for use in such a format are described below. Such assay devices are configured to perform a sandwich immunoassay for latent protein C. These assay devices will preferably further comprise a sample application zone, and a flow path from the sample application zone to a second device region comprising the first antibody conjugated to a solid phase. Other preferred assay devices of the present invention will comprise latent protein C conjugated to a solid phase and an antibody conjugated to a signal development element, wherein the antibody is sensitive for, or specifically bind, latent protein C relative to activated protein C. Such assay devices are configured to perform a competitive immunoassay for latent protein C. Still other preferred assay devices of the present invention will comprise latent protein C conjugated to a signal development element and an antibody conjugated to a solid phase, wherein the antibody is sensitive for, or specifically bind, latent protein C relative to activated protein C. Such assay devices are configured to perform a competitive immunoassay for latent protein C.

Flow of a sample along the flow path may be driven passively (e.g., by capillary, hydrostatic, or other forces that do not require further manipulation of the device once sample is applied), actively (e.g., by application of force generated via mechanical pumps, electroosmotic pumps, centrifugal force, increased air pressure, etc.), or by a combination of active and passive driving forces. Most preferably, sample applied to the sample application zone will contact both a first antibody conjugated to a solid phase and a second antibody conjugated to a signal development element along the flow path (sandwich assay format) or both latent protein C conjugated to a solid phase and an antibody conjugated to a signal development element along the flow path (competitive assay format). Additional elements, such as filters to separate plasma or serum from blood, mixing chambers, etc., may be included as required by the artisan. Exemplary devices are described in Chapter 41, entitled "Near Patient Tests: Triage® Cardiac System," in *The Immunoassay Handbook*, $2^{nd}$ ed., David Wild, ed., Nature Publishing Group, 2001, which is hereby incorporated by reference in its entirety. Other methods devices for lateral flow separation, detection, and quantification are known in, for example, U.S. Pat. Nos. 6,942,981; 5,569,608; 6,297,020; and 6,403,383 incorporated herein by reference in their entirety.

Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies as indicated by reperfusion or resolution of symptoms, differentiation of the various types of ACS, identification of the severity of the event, identification of the disease severity, and identification of the patient's outcome, including risk of future events.

A panel consisting of the markers referenced above may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers can be carried out by one skilled in the art to optimize clinical sensitivity or specificity in various clinical settings. These include, but are not limited to ambulatory, urgent care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W.B. Saunders and Company, p. 496).

The analysis of markers can be carried out in a variety of physical formats as well. For example, the use of microtiter plates or automation can be used to facilitate the processing of large numbers of test samples. Alternatively, single sample formats can be developed to facilitate immediate treatment and diagnosis in a timely fashion, for example, in ambulatory transport or emergency room settings.

IV. Kits

The invention also includes kits for the analysis of latent protein C, and optionally one or more other markers. The kit can be used for diagnosis, prognosis, and/or monitoring the treatment of SIRS. The kit comprises at least one antibody that is specific for latent protein C. The kit can also include devices and reagents for the analysis of at least one test sample and instructions for performing the assay. Kits can contain one or more means for using information obtained from immunoassays performed for a marker panel to rule in or out certain diagnoses. Other measurement strategies applicable to the methods described herein include chromatography (e.g., HPLC), mass spectrometry, receptor-based assays, and combinations of the foregoing. Some preferred kits comprise a first antibody conjugated to a solid phase and a second antibody conjugated to a signal development element, such that one or both of the first and second antibodies are sensitive for, or specifically bind, latent protein C relative to activated protein C. Other preferred kits comprise latent protein C conjugated to a solid phase and an antibody conjugated to a signal development element, such that the antibody is sensitive for, or specifically binds, latent protein C relative to activated protein C. Still other preferred kits include at least latent protein C conjugated to a signal development element and an antibody conjugated to a solid phase, such that the antibody is sensitive for, or specifically binds, latent protein C relative to activated protein C.

The instructions for use of the kit and performing the assay can be in the form of an insert and/or labeling on the box and can also include a chart or other correspondence regime correlating levels of measured label with levels of latent protein C. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

V. Antibodies

The invention provides antibodies that are sensitive for, or specifically bind latent protein C. In general, such antibodies specifically bind to an epitope that lies within or at least partly within residues 200-211 of SEQ ID NO:1. The antibodies are of course particularly useful for detecting latent protein C in the formats described above. The antibodies can be human, humanized, chimeric, or veneered. The antibodies can be monoclonal or polyclonal (see U.S. Pat. No. 6,555,310 for a description of production of high affinity polyclonal libraries). The antibodies can be used alone (for example in a competitive assay) or in combination (for example, in a sandwich assay). Two exemplary mouse monoclonal antibodies were isolated as described in Example 1 and are designated as Z1XM01701 and Z3XM01011. Although both antibodies have epitopes at least in part within the activation peptide of latent protein C, the two antibodies bind to different epitopes. The amino acid sequences of the heavy and light chain variable regions (not including signal sequences) are provided in the example. Z1XM01701 comprises a heavy chain variable region designated SEQ ID NO:4 and a light chain variable region designated SEQ ID NO:5. Z3XM01011 has a heavy chain variable region designated SEQ ID NO:6 and a light chain variable region designated SEQ ID NO:7. The antibodies can be synthesized with any light or heavy constant region (e.g., mouse IgG1 heavy chain, mouse kappa light chain) for use in detection of latent protein C, competitive binding assays or otherwise. These antibodies were found to bind to latent protein C with an affinity of at least $10^{10}$ $M^{-1}$. The antibodies did not cross react with active protein C up to about 7 µg/mL of active protein C in the sample, showing them to be specific for latent protein C. Binding of both antibodies to latent protein C is independent of calcium concentration (at least to physiological levels, i.e., up to about 90 µg/ml). Calcium-independent binding is advantageous because some patient sample may be drawn in the presence of chelators and because protein C binds to membranes in a calcium-dependent fashion. For this reason, the antibodies can be used in an assay in the presence of chelators without reducing sensitivity.

The invention further provides isolated antibodies that compete with at least one of the exemplary antibodies, monoclonal antibody Z1XM01701 or Z3XM01011, for specific binding to latent protein C. Competition can be determined by an assay in which the antibody under test inhibits specific binding of either reference antibody to an antigenic determinant on latent protein C. Numerous types of competitive binding assays are known (see Harlow and Lane, 1988, "Antibodies, A Laboratory Manual," Cold Spring Harbor Press). Typically, such an assay involves the use of latent protein C, an unlabelled test antibody and a labeled reference antibody (e.g., Z1XM01701 or Z3XM01011). Competitive inhibition is measured by determining the amount of label bound to latent protein C in the presence of the test antibody. Usually the test antibody is present in excess. Antibodies identified by the competition assay (competing antibodies) include antibodies binding to the same epitope as an exemplified antibody and antibodies binding to an adjacent epitope sufficiently proximal to the epitope bound by the reference antibody for steric hindrance to occur. Usually, when a competing antibody is present in excess, it will inhibit specific binding of a reference antibody to latent protein C by at least 50, 75 or 95%.

The invention further provide antibodies sharing a high degree of sequence identity to either Z1XM01701 or Z3XM01011. Some such antibodies include a heavy chain variable region having at least 90, 99 or 99% sequence identity to SEQ ID NO:4 and a light chain variable region having at least 90, 95 or 99% sequence identity to SEQ ID NO:5. Other antibodies include a heavy chain having at least 90, 95 or 99% sequence identity to SEQ ID NO:6 and a light chain variable region having at least 90, 95 or 99%% sequence identity to SEQ ID NO:7.

The invention further provides humanized, chimeric or veneered versions of antibodies Z1XM01701 and Z3XM01011. The invention also provides antibodies including a heavy chain that includes three CDRs from SEQ ID NO:4 and a light chain that includes three CDRs from SEQ ID NO:5. The invention also provides antibodies including a heavy chain that includes three CDRs from SEQ ID NO:6 and a light chain that includes three CDRs from SEQ ID NO:7.

The above described antibodies preferably share the characteristics of the exemplified antibodies, namely insensitivity to calcium concentration up to physiological concentration and lack of crossreactivity with active protein C (APC) in the presence of up to 7 µg/mL APC. The above antibodies preferably specifically to latent protein C with an affinity of at least $10^9$, $10^{10}$ or $10^{11}$ $M^{-1}$. The above antibodies can be used in the assays methods described above in similar fashion to the exemplified antibodies. For example, Z1XM01701 or an antibody competing with Z1 XM01701 for binding to latent protein C, and Z3XM01011 or an antibody competing with Z3XM01011 for binding to latent protein C can be used together in a sandwich assay. Z1XM01701 or an antibody competing therewith can be used alone in a competitive latent protein C detection format, as can Z3XM01011 or an antibody competing therewith.

A. General Characteristics of Antibodies

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, FUNDAMENTAL IMMUNOLOGY (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., 1987, J. Mol. Biol. 196: 901-917; Nature, 1989, 342: 878-883; and J. Mol. Biol., 1989, 186: 651-663.

B. Production

Antibodies to latent protein C can be produced by a variety of means, such as the following. One way is to purify polypeptides of interest or to synthesize the polypeptides of interest using, e.g., solid phase peptide synthesis methods well known in the art. See, e.g., *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be injected, for example, into mice or rabbits, to generate polyclonal or monoclonal antibodies. A preferred peptide consists of residues 200-211 of SEQ ID NO:1 or an immunogenic segment thereof. A few additional residues of SEQ ID NO: 1 (usually no more than 5 contiguous residues can be present at either end). One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In addition, numerous publications have reported the use of phage display technology to produce and screen libraries of polypeptides for binding to a selected target. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

C. Antibody Fragments

Antibodies of the invention include intact antibodies and binding fragments thereof. Typically, these fragments compete with the intact antibody from which they were derived for specific binding to latent protein C. Antibody fragments include separate heavy chains, light chains Fab, Fab'F(ab')2, Fv, and single chain antibodies comprises a heavy chain variable region linked to a light chain variable region via a peptide spacer.

D. Humanized, Chimeric and Human Antibodies

The antibodies can also be chimeric, humanized, veneered or human antibodies produced in mice with human immune systems. Use of such antibodies, particularly human antibodies is advantageous in avoiding false positives or negatives due to the presence of HAMA or heterophilic antibodies in the sample (U.S. Pat. No. 6,680,209). HAMA antibodies may be present in a human sample due to prior treatment of the patient from whom the sample was obtained with a mouse antibody (unrelated to the mouse antibody being used in diagnosis) or by environmental exposure to mouse antigens. Heterophilic antibodies are present in some patients as a response to certain pathogenic infections, such as Epstein Barr virus. Either HAMA or heterophilic antibodies in a sample can bind to a mouse antibody being used as a diagnostic reagent thereby generating a false positive signal. In sandwich assay formats, HAMA or heterophilic antibodies can form a bridge between immobilized and solution antibodies to generate a false positive, as in other formats. Alternatively, in a sandwich assay format, some HAMA or heterophilic antibodies may bind to the immobilized antibody without binding to the solution antibody (or vice versa) thereby preventing immobilized antibody and solution antibody from bridging to each other through an analyte and thus generating a false negative. In consequence, a significant number of assays performed on human clinical samples using mouse antibodies as the diagnostic reagent generate inaccurate results. Use of veneered, chimeric, humanized or human antibodies reduces the risk of false positives or negatives from the cause.

Chimeric antibodies are antibodies whose light and heavy chain genes have been constructed, typically by genetic engineering, from immunoglobulin gene segments belonging to different species (see, e.g., Boyce et al., Annals of Oncology 14:520-535 (2003)). For example, the variable (V) segments of the genes from a mouse monoclonal antibody may be joined to human constant (C) segments. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions substantially from a mouse-antibody, (referred to as the donor immunoglobulin). See Queen et al., Proc. Natl. Acad. Sci. USA 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539. The constant region(s), if present, are also substantially or entirely from a human immunoglobulin. Veneered antibodies are similar to humanized antibodies and are formed by replacement of exterior amino acid residues of having no effect on the ligand binding properties with human residues to reduce immunogenicity (see U.S. Pat. No. 6,797,492). Human antibodies can be obtained using e.g., phage-display methods. See, e.g., Dower et al., WO 91/17271; McCafferty et al., WO 92/01047 or transgenic mice (see Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741 (1991)). Human antibodies are selected by competitive binding experiments, or otherwise, to have the same epitope specificity as a particular mouse antibody, such as Z1XM01701 or Z3XM01011. Such antibodies are particularly likely to share the useful functional properties of the exemplified antibodies of specifically binding to latent protein C without cross-reacting with APC.

VI. Correlation with Disease

The level of latent protein C or other marker in a sample can be correlated with presence or severity of disease by comparing a measured level of latent protein C or other marker in a sample removed from a patient with a baseline level determined in a control population. The control population of normal persons is formed from individuals not known to have or be at elevated risk of having whatever disease (or other outcome) is being tested in a patient. For a patient being tested for presence or susceptibility to SIRS and/or SEPSIS a suitable control population are persons not known or suspected to be suffering from SIRS and/or sepsis. A significant departure between the measured level in a patient and baseline levels in a control population signals a positive outcome of the diagnostic test. A departure is considered significant if the measured value falls outside the range typically observed in a control population due to inherent variation between individuals and experimental error. For example, a departure can be considered significant if a measured level does not fall within the mean plus one standard deviation of levels in a control population. In some methods, a departure between a measured level and control levels is judged significant if the measured level is at least the level of the, $75^{th}$, 80th or 95th percentile of a control population. In other words, the measured level in the patient occurs in only 50%, 25%, 20% or 5% of individuals in the control population. If the measured level of an analyte does not differ significantly from baselines levels in a control population, the outcome of the diagnostic test is considered negative.

For latent protein C, a positive outcome is typically indicated by measured levels below those in a control population. For other markers, a positive outcome can be analogously indicated by measured levels either in excess or below levels in a control population. The extent of departure between a measured value and a baseline value (e.g., mean or median) in a control population also provides an indicator of the probable accuracy of the diagnosis, and/or of the severity of the disease being suffered by the patient.

If a diagnostic test for latent protein C gives a positive outcome, the patient is, at minimum, identified as being susceptible to or at risk of SIRS. The patient is then typically subject to further tests or screening. Such tests or screening can include analyses of additional analytes correlated with SIRS that have not already been tested. Such screening can also include performing biochemical tests for activity of enzymes associated with SIRS. Further tests can also include monitoring for clinical symptoms of SIRS, which include one or more of disseminated intravascular coagulation, deep vein thrombosis, severe liver disease, sepsis, vitamin K deficiency, oral anticoagulant therapy, hereditary protein C deficiency and elective surgery. Further screening can also include analyses of patient and/or family history. Further, screening can be performed for bacteria and/or fungi associated with sepsis. As a result of one or more of these screening assays, the initial diagnosis based on analyte levels can be confirmed (or otherwise), and sepsis in a patient can be identified.

The measurement of absolute values of latent protein C can show variation depending on the assay format. Thus, patient values and values for a control population are preferably determined using the same assay format. Under the assay conditions illustrated in the Example below, the concentration of latent protein C in normal patients is about 3.3 µg/ml. Thus, using this format a concentration of latent C below about 2.5 or 2 µg/mL and particularly below 1 µg/mL or 0.5 µg/mL or 0.1 µg/mL is indicative of SIRS. As is the case for many diagnostic markers the range of latent protein present in individuals with SIRS and/or sepsis is generally less than but overlaps with the range present in a control population not known to have these conditions (see FIG. 2). Such overlap does not of course preclude using a marker as a diagnostic but can result in some false positives and false negatives. The relative proportions of false positives, true positives, false negatives and true negatives can be controlled by selection of a cut off point, below which individuals are scored as diseased and above which individuals are scored as normal. If an individual has a level of latent protein C close to the cut off point, testing other diagnostic indicators is particularly useful to confirm presence or absence of disease. In the same way, if the level is considerably below normal, the necessity of the other diagnostic indicators for making a diagnosis is reduced.

Qualitative tests can be used to test for the presence of a minimum amount of latent protein C or other markers. For example, a negative test would indicate that the sample did not contain the minimum amount of latent protein C or other markers.

Alternatively, quantitative tests can be used to identify the amount of latent protein C or other markers. This type of test can be used during treatment to monitor the improvement by monitoring the increase in the amount of latent protein C and/or to monitor the increase or decrease of other markers with improvement. The latent protein C level alone or in combination with other markers can be correlated with detection of SIRS, stratification of the risk of SIRS (i.e., the lower the level, the greater the risk), and identification of the efficacy of a disease treatment, for example. The latent protein C level can indicate the severity of a disease (the lower the level of latent protein C, the more severe the disease) and can be used as a prognostic indicator. The latent protein C concentration assay can be used in the clinical management of patients with severe sepsis. The assay allows evaluation of the extent to which the endogenous protein C activation complex has been compromised, which in turn is useful in deciding whether to use protein C or APC therapeutically. Latent protein C assays can also be used in monitoring the dose, duration and efficacy of recombinant APC therapy in patients. When using the markers for identification, prognosis, diagnosis of a disease, other indications of the disease (diagnostic indicators) can be used including but not limited to: the symptoms (disseminated intravascular coagulation, deep vein thrombosis, severe liver disease, sepsis, vitamin K deficiency, oral anticoagulant therapy, hereditary protein C deficiency and elective surgery), the presence of microbes associated with sepsis, patient history.

Patients identified as having SIRS and/or sepsis are typically administered a treatment for the disorder. Treatment can be in the form of APC replacement therapy using a recombinant form of the protein. Another application of the methods lies in monitoring the condition of patients receiving treatment for SIRS. A successful treatment outcome is indicated by return of latent protein C and/or other markers from abnormal levels to or toward normal levels. Typically, such methods measure an initial value for the level of analyte before the patient has received treatment. Repeat measurements are then made over a period of time. If the initial level is elevated relative to the mean level in a control population, a significant reduction in level in subsequent measurements indicates a positive treatment outcome. Likewise, if the initial level of an analyte is reduced relative to the mean in a control population, a significant increase in measured levels relative to the initial level signals a positive treatment outcome. Subsequently measured levels are considered to have changed significantly relative to initial levels if a subsequent measured level differs by more than one standard deviation from the mean of repeat measurements of the initial level. If monitoring reveals a positive treatment outcome, the same treatment regime can be continued, or replaced with a treatment regime with a lower dosage. If monitoring reveals a negative treatment outcome, the previous treatment regime is typically modified, either by using a different therapeutic agent or increasing the dosage of the previous agent.

VII. Selecting a Treatment Regimen

Once a diagnosis is obtained, the clinician can select a treatment regimen that is compatible with the diagnosis. The skilled artisan is aware of appropriate treatments for numerous diseases discussed in relation to the methods of diagnosis described herein. See, e.g., *Merck Manual of Diagnosis and Therapy*, 17$^{th}$ Ed. Merck Research Laboratories, Whitehouse Station, N.J., 1999. With regard to SIRS, sepsis, severe sepsis, and septic shock. Recent guidelines provide additional information for the clinician. See, e.g., Dellinger et al., *Crit. Care Med.* 32: 858-73, 2004, which is hereby incorporated by reference in its entirety.

Although the present invention may be used to determine if any SIRS-related (that is, applicable to SIRS, sepsis, severe sepsis, septic shock, and MODS) treatment should be undertaken at all, the invention is preferably used to assign a particular treatment regimen from amongst two or more possible choices of SIRS-related treatment regimens. For example, in exemplary embodiments, the present invention is used to determine if subjects should receive standard therapy or early goal-directed therapy. Thus, the methods and compositions described herein may be used to select one or more of the following treatments for inclusion in a therapy regimen, 1) Administration of intravenous antibiotic therapy; 2) maintenance of a central venous pressure of 8-12 mm Hg; 3) administration of crystalloids and/or colloids, preferably to maintain such a central venous pressure; 4) maintenance of a mean arterial pressure of $\geq$65 mm Hg; 5) administration of one or more vasopressors (e.g., norepinephrine, dopamine, and/or vasopressin) and/or vasodilators (e.g., prostacyclin, pentoxifylline, N-acetyl-cysteine); 6) administration of one or more corticosteroids (e.g., hydrocortisone); 7) administration of recombinant activated protein C; 8) maintenance of a central venous oxygen saturation of $\geq$70%; 9) administration of transfused red blood cells to a hematocrit of at least 30%; 10) administration of one or more inotropics (e.g., dobutamine); and 11) administration of mechanical ventilation.

This list is not meant to be limiting. In addition, since the methods and compositions described herein provide prognostic information, the panels and markers of the present invention may be used to monitor a course of treatment. For example, improved or worsened prognostic state may indicate that a particular treatment is or is not efficacious.

EXAMPLES

The following examples serve to illustrate the present invention. These examples are in no way intended to limit the scope of the invention.

Example 1

Preparation of Antibodies Specific to Latent Protein C

Human latent protein C (Catalog # HPC 1001) and activated protein C (Catalog # APC) were purchased from Enzyme Research Labs (South Bend, Ind.). FVB mice (Taconic, Hudson, N.Y.) were immunized by subcutaneous administration of 50 µg of latent protein C mixed with 15 µg of Quil A adjuvant (Accurate Chemical and Scientific Corp, Westbury, N.Y.) in PBS, pH 7.4 on day 0. Two subsequent immunizations were performed on days 14 and 28 using the antigen mixed with Quil A. On day 36, blood samples were obtained from the mice by retro-orbital plexus bleeds and serum IgG responses were determined by ELISA using biotinylated latent protein C and activated protein C immobilized in separate wells via neutravidin (Reacti-Bind™ NeutrAvidin™-Coated Polystyrene Plates, Pierce, Rockford, Ill.). Two consecutive boosts of 50 µg of protein were administered via intraperitoneal injection on days 42 and 43. On day 45, the mice were sacrificed and spleens were harvested for RNA isolation.

Phage libraries displaying antibodies (as Fab fragments) on phage fd gene III protein were made from the RNA isolated from the immunized mice and screened using standard methodologies (see, e.g., U.S. Pat. No. 6,057,098, WO 03/068956, each of which is hereby incorporated by reference in its entirety, and references cited therein). The phage samples were panned with biotinylated latent protein C ($1\times10^{-8}$M) for 2 rounds, then the individual phage samples were pooled and the sample was panned at $1\times10^{-9}$M biotinylated latent protein C for one round. To get antibodies specific to latent protein C, two rounds of panning were performed using biotinylated latent protein C at $1\times10^{-10}$M in the presence of active protein C at $6.6\times10^{-7}$M (for round 4) and $1.3\times10^{-6}$ M (for round 5). The antibodies specific for latent protein C (relative to active protein C) were subcloned into a pBR322 expression vector having an arabinose promoter, and the antibodies were analyzed for binding to latent protein C.

One of the monoclonal antibodies specific to latent protein C (designated Z1XM 01701, also known as SE61z1zm-01071) was selected expressed, purified and biotinylated as described in U.S. Pat. No. 6,057,098. An additional round of panning was performed with the phage derived from the 5$^{th}$ round of panning above, and the antibody sequences obtained from the resulting phage were subcloned into a pBR322 expression vector. The antibodies from this library yielded antibodies specific to latent protein C (relative to active protein C) that bound at a different epitope from Z1XM01701. One of these antibodies was designated Z3XM01011.

The sequence of the heavy and light chain variable regions of Z1XM01701 are provided as SEQ ID NOs:4 and 5 respectively. Likewise, the heavy and light chain variable region of Z3XM01011 are designated SEQ ID NOs. 6 and 7 respectively. All variable regions are shown without signal sequences (i.e., as mature variable regions).

```
gaagtgatgctggtggagtctggggggaggcttagtgaagcctggaggt
 E   V   M   L   V   E   S   G   G   G   L   V   K   P   G   G
ccctgaaactctcctgtgcagcctctggattcactttcagtaactatgc
 S   L   K   L   S   C   A   A   S   G   F   T   F   S   N   Y   A
catgtctttgggttcgccagactccggcgaagaggctggagtgggtcgca
 M   S   W   V   R   Q   T   P   A   K   R   L   E   W   V
actattagtggtggtggtggtaacacctactatccagacagtgtgaagg
 T   I   S   G   G   G   N   T   Y   Y   P   D   S   V   K
gccgattcaccatctccagagacaatgccaagaacaccctgtacctgca
 G   R   F   T   I   S   R   D   N   A   K   N   T   L   Y   L   Q
aatgagcagtctgaggtctgaggacacggccttgtattattgtgcaaga
 M   S   S   L   R   S   E   D   T   A   L   Y   Y   C   A   R
catcccaataggttcgagactgctgtggactactggggtcaaggaacct
 H   P   N   R   F   E   T   A   V   D   Y   W   G   Q   G   T
cagtcatcgtctcctca
 S   V   I   V   S   S
(amino acid) SEQ ID NO:4 (nucleotide) SEQ ID NO:8 caaattgttctcacccagtctccagcaatcctgtctgcatctccgggag
 Q   I   V   L   T   Q   S   P   A   I   L   S   A   S   P   G
agaaggtcacaatgacttgcagggccagctcaagtgttagttccgtgca
 E   K   V   T   M   T   C   R   A   S   S   S   V   S   S   V   H
ctggtaccagcagaagccaggatcctcccccaaaccctggatttatgcc
 W   Y   Q   Q   K   P   G   S   S   P   K   P   W   I   Y   A
acatccaacctggcttctggagtccctactcgcttcagtggcggtgggt
 T   S   N   L   A   S   G   V   P   T   R   F   S   G   G
ctgggacctcttactctctcacaatcagcagagtggaggctgaagatgc
 S   G   T   S   Y   S   L   T   I   S   R   V   E   A   E   D   A
tgccacttattcctgccagcagtggagtagtgacccacccacgttcgga
 A   T   Y   S   C   Q   Q   W   S   S   D   P   P   T   F   G
```

-continued
```
gggggaccaagctggagataaaa
 G  G  T  K  L  E  I  K
(amino acid) SEQ ID NO:5 (nucleotide) SEQ ID NO:9 gaggtccagcttcagcagtcaggacctggcctagtggagccctcacaga
 E  V  Q  L  Q  Q  S  G  P  G  L  V  E  P  S  Q
gcctgtccatcacctgcacagtctctggtttctcattaaggagctatgg
 S  L  S  I  T  C  T  V  S  G  F  S  L  R  S  Y  C
cgtacactgggttcgccagtctccaagaaaggggtctggagtggctggga
 V  H  N  V  R  Q  S  P  R  K  G  L  E  W  L  G
gggatatggagtggtggaaggatagactataatgcagcttacatatcca
 G  I  W  S  G  G  R  I  D  Y  N  A  A  Y  I  S
gactgaccatcaacaaggacaattccaagagccaagttttctttaaaat
 R  L  T  I  N  K  D  N  S  K  S  Q  V  F  F  K  M
gaacagtctgcaagctgatgacacagccatatattactgtgtcagaaag
 N  S  L  Q  A  D  D  T  A  I  Y  Y  C  V  R  K
gcgatcgacttgggagattattatggtatggactattggggtcaaggaa
 A  I  D  L  G  D  Y  Y  G  M  D  Y  W  G  Q  G
cctcagtcaccgtctcttct
 T  S  V  T  V  S  S
(amino acid) SEQ ID NO:4 (nucleotide) SEQ ID NO:10 gacattgtgatgacccagttctcacaaattctgtccacatcagtaggag
 D  I  V  M  T  Q  F  S  Q  I  L  S  T  S  V  G
acagggtcagcatcacctgcaaggccagtcaggatgtgggtactgctgt
 D  R  V  S  I  T  C  K  A  S  Q  D  V  G  T  A  V
agcctggtatcaacagaaaccaggacaatctcctaaactactaatttac
 A  W  Y  Q  Q  K  P  G  Q  S  P  K  L  L  I  Y
tgggcatccacccggcacactggagtccctggtcgcttcacaggcagtg
 W  A  S  T  R  H  T  G  V  P  G  R  F  T  G  S
gatctgggacagatttcactctcaccattatcagtgtgcagtctgaaga
 G  S  G  T  D  F  T  L  T  I  I  S  V  Q  S  E  D
cttggcagattatttctgtcagcaatatagcagctatccgacgttcggt
 L  A  D  Y  F  C  Q  Q  Y  S  S  Y  P  T  F  G
ggaggcaccaagctggaaatcaaa
 G  G  T  K  L  E  I  K
(amino acid) SEQ ID NO:7 (nucleotide) SEQ ID NO:11
```

These antibodies were tested and found to exhibit no cross-reactivity in the assay shown in Example 4 up to 7 µg/mL active protein C. Because levels of active protein C are usually substantially less than this in patient samples, these antibodies can be used to identify the presence and amount of latent protein C without detecting active protein C. Further, the antibodies were tested and found not to be calcium sensitive. Lack of calcium sensitivity is useful because some samples for assays may be drawn in the presence of chelators and some are not and because protein C binds to membranes in a calcium dependent fashion. Because the antibody can be used in the presence or absence of calcium, it can be used with any sample (without treatment of the sample to remove calcium) to assay for latent protein C.

Example 2

Microtiter Plate-Based Biochemical Analyses

General methods for performing sandwich immunoassays in microtiter plates are as follows: a monoclonal antibody directed against a selected analyte is biotinylated using N-hydroxysuccinimide biotin (NHS-biotin) at a ratio of about 5 NHS-biotin moieties per antibody. The antibody-biotin conjugate is then added to wells of a standard avidin 384 well microtiter plate, and antibody conjugate not bound to the plate is removed. This forms the "anti-marker" in the microtiter plate. Another monoclonal antibody directed against the same analyte is conjugated to alkaline phosphatase, for example using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Biotinylated antibodies are pipetted into microtiter plate wells previously coated with avidin and incubated for 60 min. The solution containing unbound antibody is removed, and the wells washed with a wash buffer, consisting of 20 mM borate (pH 7.42) containing 150 mM NaCl, 0.1% sodium azide, and 0.02% Tween-20. The plasma samples (10 µL) containing added HAMA inhibitors are pipeted into the microtiter plate wells, and incubated for 60 min. The sample is then removed and the wells washed with a wash buffer. The antibody-alkaline phosphatase conjugate is then added to the wells and incubated for an additional 60 min, after which time, the antibody conjugate was removed and the wells washed with a wash buffer. A substrate, (AttoPhos®, Promega, Madison, Wis.) is added to the wells, and the rate of formation of the fluorescent product is related to the concentration of the analyte in the sample tested.

For competitive immunoassays in microtiter plates, a murine monoclonal antibody directed against a selected analyte is added to the wells of a microtiter plate and immobilized by binding to goat anti-mouse antibody that is pre-absorbed to the surface of the microtiter plate wells (Pierce, Rockford, Ill.). Any unbound murine monoclonal antibody is removed after a 60 minute incubation. This forms the "anti-marker" in the microtiter plate. A purified polypeptide that is either the same as or related to the selected analyte, and that can be bound by the monoclonal antibody, is biotinylated as described above for the biotinylation of antibodies. This biotinylated polypeptide is mixed with the sample in the presence of HAMA inhibitors, forming a mixture containing both exogenously added biotinylated polypeptide and any unlabeled analyte molecules endogenous to the sample. The amount of the monoclonal antibody and biotinylated marker added depends on various factors and is titrated empirically to obtain a satisfactory dose-response curve for the selected analyte.

This mixture is added to the microtiter plate and allowed to react with the murine monoclonal antibody for 120 minutes. After the 120 minute incubation, the unbound material is removed, and Neutralite-Alkaline Phosphatase (Southern Biotechnology; Birmingham, Ala.) is added to bind to any immobilized biotinylated polypeptide. Substrate (as described above) is added to the wells, and the rate of formation of the fluorescent product is related to the amount of biotinylated polypeptide bound, and therefore is inversely related to the endogenous amount of the analyte in the specimen.

Example 3

Microfluidic Device-Based Biochemical Analyses

Immunoassays may also be performed using microfluidic devices essentially as described in Chapter 41, entitled "Near Patient Tests: Triage® Cardiac System," in *The Immunoassay Handbook*, $2^{nd}$ ed., David Wild, ed., Nature Publishing Group, 2001.

For sandwich immunoassays, a plasma sample is added to the microfluidic device that contains all the necessary assay reagents, including HAMA inhibitors, in dried form. The plasma passes through a filter to remove particulate matter. Plasma enters a "reaction chamber" by capillary action. This reaction chamber contains fluorescent latex particle-antibody conjugates (hereafter called FETL-antibody conjugates) appropriate to an analyte of interest, and may contain FETL-antibody conjugates to several selected analytes. The FETL-antibody conjugates dissolve into the plasma to form a reaction mixture, which is held in the reaction chamber for an incubation period (about a minute) to allow the analyte(s) of interest in the plasma to bind to the antibodies. After the incubation period, the reaction mixture moves down the detection lane by capillary action. Antibodies to the analyte(s) of interest are immobilized in discrete capture zones on the surface of a "detection lane." Analyte/antibody-FETL complexes formed in the reaction chamber are captured on an appropriate detection zone to form a sandwich complex, whereas unbound FETL-antibody conjugates are washed from the detection lane into a waste chamber by excess plasma. The amount of analyte/antibody-FETL complex bound on a capture zone is quantified with a fluorometer (Triage® MeterPlus, Biosite Incorporated) and is related to the amount of the selected analyte in the plasma specimen.

For competitive immunoassays, the procedure and process is similar to that described for sandwich immunoassays, with the following exceptions. In one configuration, fluorescent latex particle-marker (FETL-marker) conjugates are provided in the reaction chamber, and are dissolved in the plasma to form a reaction mixture. This reaction mixture contains both the unlabeled analyte endogenous to the sample, and the FETL-marker conjugates. When the reaction mixture contacts the capture zone for a analyte of interest, the unlabeled endogenous analyte and the FETL-marker conjugates compete for the limited number of antibody binding sites. Thus, the amount of FETL-marker conjugate bound to the capture zone is inversely related to the amount of analyte endogenously present in the plasma specimen. In another configuration, antibody-FETL conjugates are provided in the reaction chamber as described above for sandwich assays. In this configuration, the capture zone contains immobilized marker on the surface of the detection lane. Free antibody-FETL conjugates bind to this immobilized marker on the capture zone, whereas antibody-FETL conjugates bound to an analyte of interest do not bind as readily or at all to this immobilized marker. Again, the amount of FETL captured in the zone is inversely related to the amount of the selected analyte in the plasma specimen. One skilled in the art will recognize that either configuration may be used depending on the characteristics and concentrations of the selected analyte(s).

Example 4

Latent Protein C Assay

The specificity of the latent protein C sandwich immunoassay was studied using standard immunoassay techniques. Samples were prepared by adding latent protein C (Enzyme Research Laboratories, South Bend, Ind.; catalog#: HPC 1001) and activated protein C (Enzyme Research Laboratories, South Bend, Ind.; catalog#: APC) to protein C-deficient plasma pool. The prepared sample was added to a microfluidic assay device prepared as described in Example 3 and in "Near Patient Tests: Triage® Cardiac System," in *The Immunoassay Handbook*, $2^{nd}$ ed., David Wild, ed., Nature Publishing Group, 2001, which is hereby incorporated in its entirety.

In one configuration of a competitive assay, fluorescent latex particles (FETL) conjugated with antibody specific for latent protein C were dried in a reaction chamber. Upon addition of a blood sample to the assay device, plasma was separated using a filter integral to the device, and the antibody-detectable label conjugate becomes dissolved in plasma exiting the filter to form the reaction mixture. This reaction mixture contains both the native latent protein C present in the plasma and the antibody conjugated to the FETL. When the reaction mixture contacts a detection zone to which is immobilized latent protein C, the native latent protein C and the protein C conjugated to the solid phase compete for binding of the antibody-detectable label conjugate, so that the amount of FETL-antibody conjugates bound to the detection zone inversely relates to the amount of native latent protein C present in the plasma specimen.

FIG. 1 shows that the immunoassay response inversely correlates with the amount of latent protein C added to protein C-deficient plasma, whereas the assay does not exhibit significant cross-reactivity with APC in the tested concentration range. In the figure, the error bars represent the standard error of the mean (SEM; N=4). This result confirms the specificity of produced antibodies for the latent form of protein C, the normal range of which is 3-6 µg/mL (Aird, *Best Practive & Research Clinical Haematology* 17: 161-182, 2004).

Example 5

Latent Protein C in Systemic Inflammatory Response Syndrome

Figure 2:
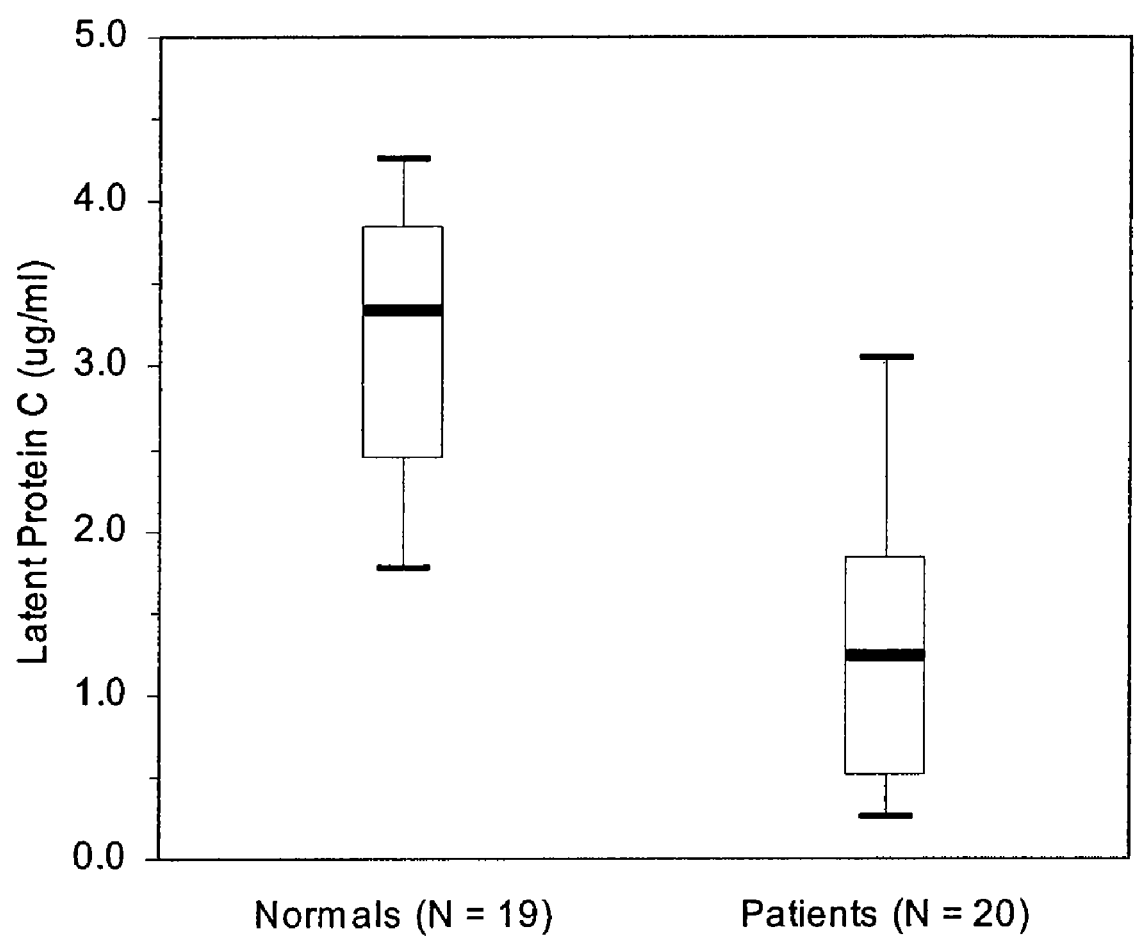
FIG. 2 shows relative latent protein C levels measured in 19 normal healthy control subjects and 20 patient samples collected from adult patients presenting to hospital emergency departments with systemic inflammatory response syndrome (SIRS) and SIRS with suspected sepsis.

Plasma samples were measured using the immunoassay specific for latent protein C described in Example 4. The control group consists of 19 normal samples that were collected from apparently healthy donors by Golden West Biologicals (Temecula, Calif.). The diseased group consists of 20 patient samples collected from adult patients presenting to hospital emergency departments (ED) with systemic inflammatory response syndrome (SIRS) and SIRS with suspected sepsis. The plasma level of latent protein C was measurable in all 39 samples with median values of 3.3 µg/mL (control group) and 1.2 µg/mL (diseased group). The latent protein C levels in the diseased group were significantly lower than in the control group (FIG. 2; p<0.0001). The lowest and highest horizontal lines of each plot represents the values of $10^{th}$ and $90^{th}$ percentiles. The highest and lowest edges of each box are $25^{th}$ and $75^{th}$ percentiles. The slightly thicker horizontal line in the middle of the box represents the value of the median. Receiver operating characteristic (ROC) analysis indicated diagnostic utility of the immunoassay in differentiating healthy subjects from patients who may exhibit coagulopathy (ROC Area=0.87; 95% Confidence Interval 0.76-0.98).

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification (including sequence database citations) are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations that is/are not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Unless otherwise apparent from the context any embodiment, element, feature or process step can be used in combination with any other.

Other embodiments are set forth within the following claims.

---

What is claimed is:

1. An immunoassay method for detection of latent protein C in a sample of bodily fluid obtained from a patient, comprising:

contacting the sample of bodily fluid with an antibody that specifically binds to latent protein C, wherein the antibody does not significantly cross-react with activated protein C, and wherein the antibody is a monoclonal antibody that competes with an antibody comprising a heavy chain variable region having an amino acid sequence of SEQ ID NO:6 and a light chain variable region having an amino acid sequence of SEQ ID NO:7 for specific binding to latent protein C;

detecting an amount of antibody bound to latent protein C present in the sample; and calculating the amount of latent protein C present in the sample based on the amount of antibody detected.

2. The method of claim 1, wherein the patient is a human.

3. The method of claim 2, wherein the patient is a patient having or suspected of having systemic inflammatory response syndrome (SIRS).

4. The method of claim 1, wherein the immunoassay method is a sandwich immunoassay method.

5. The method of claim 4, wherein the contacting step comprises contacting the test sample with a first antibody conjugated to a solid phase and a second antibody conjugated to a signal development element, wherein one or both of the first and second antibodies are sensitive for latent protein C relative to activated protein C, and wherein the signal generated is indicative of protein bound to both the first and second antibodies.

6. The method of claim 1, wherein the immunoassay method is a competitive immunoassay method.

7. The method of claim 6, wherein the contacting step comprises contacting the test sample with latent protein C conjugated to a solid phase and an antibody conjugated to a signal development element, wherein the antibody is sensitive for latent protein C relative to activated protein C.

8. The method of claim 6, wherein the contacting step comprises contacting the test sample with latent protein C conjugated to a signal development element and an antibody conjugated to a solid phase wherein the antibody is sensitive for latent protein C relative to activated protein C.

9. The method of claim 1, wherein the signal is generated electrochemically.

10. The method of claim 9, wherein the signal is generated using an antibody-based biosensor.

11. The method of claim 1, wherein the signal is generated optically.

12. The method of claim 11, wherein the signal is generated using a fluorometer.

13. The method of claim 1, wherein the sample of bodily fluid is a blood, serum, or plasma sample.

14. The method of claim 1, wherein the immunoassay is configured to generate a detectable signal when latent protein C having the sequence depicted by residues 43-461 of SEQ ID NO:1 is present at a concentration between 1 µg/mL and 5 µg/mL.

15. The method of claim 1, wherein the immunoassay is configured to generate a detectable signal from 3 µg/mL of latent protein C having the sequence depicted by residues 43-461 of SEQ ID NO: 1 that is at least about 5 fold greater than a signal obtained from an equimolar amount of active protein C.

16. The method of claim 1, wherein the immunoassay is configured to generate a detectable signal from 3 µg/mL of latent protein C having the sequence depicted by residues 43-461 of SEQ ID NO: 1 that is at least about 10 fold greater than a signal obtained from an equimolar amount of active protein C.

17. The method of claim 1, wherein the immunoassay is configured to generate a detectable signal from 3 µg/mL of latent protein C having the sequence depicted by residues 43-461 of SEQ ID NO: 1 that is at least about 25 fold greater than a signal obtained from an equimolar amount of active protein C.

18. The method of claim 1, wherein the immunoassay is configured to generate a detectable signal from 3 µg/mL of latent protein C having the sequence depicted by residues 43-461 of SEQ ID NO: 1 that is at least about 5 fold greater than a signal obtained from an equimolar amount of active protein C, and to generate a detectable signal when latent protein C having the sequence depicted by residues 43-461 of SEQ ID NO: 1 is present at a concentration between 1 µg/mL and 5 µg/mL.

19. The method of claim 1, wherein the sample contains a chelating agent.

20. The method of claim 17, wherein the antibody is a human, humanized, chimeric or veneered antibody.

21. The method of claims 1 or 13, wherein the activated protein C is endogenous to the patient from which the sample was obtained.

22. The method of claims 1 or 13, wherein the activated protein C has been administered to the patient as a pharmaceutical preparation.

23. The method of claim 22, wherein the pharmaceutical preparation is drotrecogin alfa.

* * * * *

UNITED STATES PATENT AND TRADEMARK OFFICE
CERTIFICATE OF CORRECTION

PATENT NO.       : 7,655,428 B2                                                Page 1 of 1
APPLICATION NO. : 11/614836
DATED            : February 2, 2010
INVENTOR(S)      : Valkirs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 434 days.

Signed and Sealed this

Twenty-eighth Day of December, 2010

David J. Kappos
*Director of the United States Patent and Trademark Office*

SEQUENCE LISTING

<160> NUMBER OF SEQ ID NOS: 11

<210> SEQ ID NO 1
<211> LENGTH: 461
<212> TYPE: PRT
<213> ORGANISM: Homo sapiens

<400> SEQUENCE: 1

```
Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Glu Arg
                20                  25                  30

Ala His Gln Val Leu Arg Ile Arg Lys Arg Ala Asn Ser Phe Leu Glu
            35                  40                  45

Glu Leu Arg His Ser Ser Leu Glu Arg Glu Cys Ile Glu Glu Ile Cys
        50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
                100                 105                 110

Asp Gly Ile Gly Ser Phe Ser Cys Asp Cys Arg Ser Gly Trp Glu Gly
            115                 120                 125

Arg Phe Cys Gln Arg Glu Val Ser Phe Leu Asn Cys Ser Leu Asp Asn
            130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
                180                 185                 190

Lys Arg Ser His Leu Lys Arg Asp Thr Glu Asp Gln Glu Asp Gln Val
            195                 200                 205

Asp Pro Arg Leu Ile Asp Gly Lys Met Thr Arg Arg Gly Asp Ser Pro
210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
                260                 265                 270

Trp Glu Lys Trp Glu Leu Asp Leu Asp Ile Lys Glu Val Phe Val His
            275                 280                 285

Pro Asn Tyr Ser Lys Ser Thr Thr Asp Asn Asp Ile Ala Leu Leu His
            290                 295                 300

Leu Ala Gln Pro Ala Thr Leu Ser Gln Thr Ile Val Pro Ile Cys Leu
305                 310                 315                 320
```

```
Pro Asp Ser Gly Leu Ala Glu Arg Glu Leu Asn Gln Ala Gly Gln Glu
            325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
            355                 360                 365

Pro His Asn Glu Cys Ser Glu Val Met Ser Asn Met Val Ser Glu Asn
            370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
            405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
            435                 440                 445

Ile Arg Asp Lys Glu Ala Pro Gln Lys Ser Trp Ala Pro
            450                 455                 460

<210> SEQ ID NO 2
<211> LENGTH: 108
<212> TYPE: PRT
<213> ORGANISM: Homo sapiens

<400> SEQUENCE: 2

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
                100                 105

<210> SEQ ID NO 3
<211> LENGTH: 134
<212> TYPE: PRT
<213> ORGANISM: Homo sapiens

<400> SEQUENCE: 3

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80
```

```
Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
            115                 120                 125

Lys Val Leu Arg Arg His
        130

<210> SEQ ID NO 4
<211> LENGTH: 120
<212> TYPE: PRT
<213> ORGANISM: Artificial Sequence
<220> FEATURE:
<223> OTHER INFORMATION: Heavy chain variable revion of moAb Z1XM1701.

<400> SEQUENCE: 4

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Ala Lys Arg Leu Glu Trp Val
        35                  40                  45

Ala Thr Ile Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg His Pro Asn Arg Phe Glu Thr Ala Val Asp Tyr Trp Gly Gln
            100                 105                 110

Gly Thr Ser Val Ile Val Ser Ser
        115                 120

<210> SEQ ID NO 5
<211> LENGTH: 106
<212> TYPE: PRT
<213> ORGANISM: Artificial Sequence
<220> FEATURE:
<223> OTHER INFORMATION: Light chain variable revion of moAb Z1XM1701.

<400> SEQUENCE: 5

Gln Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Ser Val
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Gly
    50                  55                  60

Gly Ser Gly Thr Ser Tyr Ser Leu Thr Ile Ser Arg Val Glu Ala Glu
65                  70                  75                  80

Asp Ala Ala Thr Tyr Ser Cys Gln Gln Trp Ser Ser Asp Pro Pro Thr
                85                  90                  95

Phe Gly Gly Gly Thr Lys Leu Glu Ile Lys
            100                 105

<210> SEQ ID NO 6
```

<211> LENGTH: 121
<212> TYPE: PRT
<213> ORGANISM: Artificial Sequence
<220> FEATURE:
<223> OTHER INFORMATION: Heavy chain variable revion of moAb Z3XM1011.

<400> SEQUENCE: 6

```
Glu Val Gln Leu Gln Gln Ser Gly Pro Gly Leu Val Glu Pro Ser Gln
1               5                   10                  15
Ser Leu Ser Ile Thr Cys Thr Val Ser Gly Phe Ser Leu Arg Ser Tyr
            20                  25                  30
Gly Val His Trp Val Arg Gln Ser Pro Arg Lys Gly Leu Glu Trp Leu
        35                  40                  45
Gly Gly Ile Trp Ser Gly Gly Arg Ile Asp Tyr Asn Ala Ala Tyr Ile
    50                  55                  60
Ser Arg Leu Thr Ile Asn Lys Asp Asn Ser Lys Ser Gln Val Phe Phe
65                  70                  75                  80
Lys Met Asn Ser Leu Gln Ala Asp Asp Thr Ala Ile Tyr Tyr Cys Val
                85                  90                  95
Arg Lys Ala Ile Asp Leu Gly Asp Tyr Tyr Gly Met Asp Tyr Trp Gly
            100                 105                 110
Gln Gly Thr Ser Val Thr Val Ser Ser
        115                 120
```

<210> SEQ ID NO 7
<211> LENGTH: 106
<212> TYPE: PRT
<213> ORGANISM: Artificial Sequence
<220> FEATURE:
<223> OTHER INFORMATION: Light chain variable revion of moAb Z3XM01011.

<400> SEQUENCE: 7

```
Asp Ile Val Met Thr Gln Phe Ser Gln Ile Leu Ser Thr Ser Val Gly
1               5                   10                  15
Asp Arg Val Ser Ile Thr Cys Lys Ala Ser Gln Asp Val Gly Thr Ala
            20                  25                  30
Val Ala Trp Tyr Gln Gln Lys Pro Gly Gln Ser Pro Lys Leu Leu Ile
        35                  40                  45
Tyr Trp Ala Ser Thr Arg His Thr Gly Val Pro Gly Arg Phe Thr Gly
    50                  55                  60
Ser Gly Ser Gly Thr Asp Phe Thr Leu Thr Ile Ile Ser Val Gln Ser
65                  70                  75                  80
Glu Asp Leu Ala Asp Tyr Phe Cys Gln Gln Tyr Ser Ser Tyr Pro Thr
                85                  90                  95
Phe Gly Gly Gly Thr Lys Leu Glu Ile Lys
            100                 105
```

<210> SEQ ID NO 8
<211> LENGTH: 360
<212> TYPE: DNA
<213> ORGANISM: Artificial Sequence
<220> FEATURE:
<223> OTHER INFORMATION: Heavy chain variable revion of moAb Z1XM01701.

<400> SEQUENCE: 8

```
gaagtgatgc tggtggagtc tgggggaggc ttagtgaagc ctggagggtc cctgaaactc      60
tcctgtgcag cctctggatt cactttcagt aactatgcca tgtcttgggt tcgccagact     120
ccggcgaaga ggctggagtg gtcgcaact attagtggtg gtggtggtaa cacctactat     180
```

```
ccagacagtg tgaagggccg attcaccatc tccagagaca atgccaagaa caccctgtac    240
ctgcaaatga gcagtctgag gtctgaggac acggccttgt attattgtgc aagacatccc    300
aataggttcg agactgctgt ggactactgg ggtcaaggaa cctcagtcat cgtctcctca    360
```

<210> SEQ ID NO 9
<211> LENGTH: 318
<212> TYPE: DNA
<213> ORGANISM: Artificial Sequence
<220> FEATURE:
<223> OTHER INFORMATION: Light chain variable revion of moAb Z1XM01701.

<400> SEQUENCE: 9

```
caaattgttc tcacccagtc tccagcaatc ctgtctgcat ctccgggaga aaggtcaca     60 atgacttgca gggccagctc aagtgttagt tccgtgcact ggtaccagca gaagccagga   120
tcctccccca aaccctggat ttatgccaca tccaacctgg cttctggagt ccctactcgc   180
ttcagtggcg gtgggtctgg gacctcttac tctctcacaa tcagcagagt ggaggctgaa   240
gatgctgcca cttattcctg ccagcagtgg agtagtgacc cacccacgtt cggaggggg    300 accaagctgg agataaaa                                                 318
```

<210> SEQ ID NO 10
<211> LENGTH: 363
<212> TYPE: DNA
<213> ORGANISM: Artificial Sequence
<220> FEATURE:
<223> OTHER INFORMATION: Heavy chain variable revion of moAb Z3XM01011.

<400> SEQUENCE: 10

```
gaggtccagc ttcagcagtc aggacctggc ctagtggagc cctcacagag cctgtccatc    60
acctgcacag tctctggttt ctcattaagg agctatggcg tacactgggt tcgccagtct   120
ccaagaaagg gtctggagtg gctgggaggg atatggagtg gtggaaggat agactataat   180
gcagcttaca tatccagact gaccatcaac aaggacaatt ccaagagcca gttttctttt   240
aaaatgaaca gtctgcaagc tgatgacaca gccatatatt actgtgtcag aaaggcgatc   300
gacttgggag attattatgg tatggactat tggggtcaag gaacctcagt caccgtctct   360
tct                                                                 363
```

<210> SEQ ID NO 11
<211> LENGTH: 318
<212> TYPE: DNA
<213> ORGANISM: Artificial Sequence
<220> FEATURE:
<223> OTHER INFORMATION: Light chain variable revion of moAb Z3XM01011.

<400> SEQUENCE: 11

```
gacattgtga tgacccagtt ctcacaaatt ctgtccacat cagtaggaga cagggtcagc    60
atcacctgca aggccagtca ggatgtgggt actgctgtag cctggtatca acagaaacca   120
ggacaatctc ctaaactact aatttactgg gcatccaccc ggcacactgg agtccctggt   180
cgcttcacag gcagtggatc tgggacagat ttcactctca ccattatcag tgtgcagtct   240
gaagacttgg cagattattt ctgtcagcaa tatagcagct atccgacgtt cggtggaggc   300
accaagctgg aaatcaaa                                                 318
```